(12) United States Patent
Blumberg et al.

(10) Patent No.: US 7,067,129 B2
(45) Date of Patent: Jun. 27, 2006

(54) RECEPTOR SPECIFIC TRANSEPITHELIAL TRANSPORT IN THERAPEUTICS

(75) Inventors: Richard S. Blumberg, Chestnut Hill, MA (US); Neil E. Simister, Wellesley, MA (US); Wayne I. Lencer, Jamaica Plain, MA (US)

(73) Assignees: The Brigham and Woman's Hospital, Inc., Boston, MA (US); Brandeis University, Waltham, MA (US)

( * ) Notice: Subject to any disclaimer, the term of this patent is extended or adjusted under 35 U.S.C. 154(b) by 0 days.

(21) Appl. No.: 10/215,298

(22) Filed: Aug. 8, 2002

(65) Prior Publication Data

US 2003/0012789 A1 Jan. 16, 2003

Related U.S. Application Data

(60) Division of application No. 09/122,144, filed on Jul. 24, 1998, now Pat. No. 6,485,726, which is a continuation-in-part of application No. 08/899,856, filed on Jul. 24, 1997, now Pat. No. 6,030,613, which is a continuation-in-part of application No. 08/578,171, filed on Dec. 29, 1995, now abandoned, which is a continuation-in-part of application No. 08/374,159, filed on Jan. 17, 1995, now Pat. No. 6,086,875.

(51) Int. Cl.
*A61K 39/395* (2006.01)

(52) U.S. Cl. ................. 424/134.1; 424/45; 424/46; 424/84; 424/85.1; 424/85.2; 424/85.4; 424/85.5; 424/85.6; 424/85.7; 424/178.1; 424/809; 514/2; 514/8; 530/387.3; 530/391.1; 530/866

(58) Field of Classification Search ......... 424/84–85.7, 424/134.1, 178.1, 804, 45, 46; 514/2, 8; 530/350, 387.3, 391.1, 395, 399, 402, 866
See application file for complete search history.

(56) References Cited

U.S. PATENT DOCUMENTS

| | | | |
|---|---|---|---|
| 4,261,973 A | 4/1981 | Lee et al. | |
| 4,650,675 A | 3/1987 | Borel et al. | |
| 4,902,495 A | 2/1990 | Kaliner et al. | |
| 5,116,964 A | 5/1992 | Capon et al. | |
| 5,120,525 A | 6/1992 | Goldenberg | |
| 5,169,627 A | 12/1992 | Cunningham-Rundles | |
| 5,277,894 A | 1/1994 | Strauss et al. | |
| 5,349,053 A | 9/1994 | Landolfi | |
| 5,354,934 A | 10/1994 | Pitt et al. | |
| 5,428,130 A | 6/1995 | Capon et al. | |
| 5,455,165 A | 10/1995 | Capon et al. | |
| 5,514,582 A | 5/1996 | Capon et al. | |
| 5,534,496 A | 7/1996 | Lee et al. | |
| 5,541,087 A | 7/1996 | Lo et al. | |
| 5,565,335 A | 10/1996 | Capon et al. | |
| 5,609,846 A | 3/1997 | Goldenberg | |
| 5,658,762 A | 8/1997 | Zanetti et al. | |
| 5,698,679 A | 12/1997 | Nemazee | |
| 5,726,044 A | 3/1998 | Lo et al. | |
| 5,843,397 A | 12/1998 | Goldenberg | |
| 6,126,938 A * | 10/2000 | Guy et al. | ............... 424/184.1 |
| 2002/0192222 A1 | 12/2002 | Blumberg et al. | |
| 2003/0235536 A1 | 12/2003 | Blumberg et al. | |
| 2004/0063912 A1 | 4/2004 | Blumberg et al. | |

FOREIGN PATENT DOCUMENTS

| | | | |
|---|---|---|---|
| AU | 8821725 | * | 3/1989 |
| CA | 2045869 | | 6/1991 |
| CA | 2045869 | * | 12/1991 |
| EP | 0 305 967 A2 | | 2/1987 |
| EP | 0 580 171 | | 1/1994 |
| WO | WO 86/06635 | | 11/1986 |
| WO | WO 91/07987 | | 6/1991 |
| WO | WO 91/08298 | | 6/1991 |
| WO | WO 91/08773 | | 6/1991 |
| WO | WO 92/05793 | | 4/1992 |
| WO | WO 93/17715 | | 9/1993 |
| WO | WO 93/19660 | | 10/1993 |
| WO | WO 93/20834 | | 10/1993 |
| WO | WO 93/21906 | | 11/1993 |
| WO | WO 94/14437 | | 7/1994 |
| WO | WO 94/15635 | | 7/1994 |
| WO | WO 96/22024 | | 7/1996 |
| WO | 9834645 | * | 8/1998 |
| WO | WO 98/34645 | | 8/1998 |
| WO | WO 99/04813 | | 2/1999 |

OTHER PUBLICATIONS

Ahouse et al., J Immunol 151:6076-6088 (1993).
Berryman et al., J Histochem Cytochem 38(2):159-170 (1990).
Borel H et al., J Immunol Methods 126:159-168 (Sep. 20, 1990).
Burmeister WP et al., Nature 372:379-383 (1994).
Canfield et al., J Exp Med 173:1483-1491 (1991).
Czerkinsky et al., Infect Immun 57:1072-1077 (1989).
Dertzbaugh et al., CRC Press:119-131 (1990).
Elson et al., J Immunol 132:2736-2741 (1984).
Elson et al., J Immunol 133:2892-2897 (1984).

(Continued)

*Primary Examiner*—David Saunders
(74) *Attorney, Agent, or Firm*—Wolf, Greenfield & Sacks, P.C.

(57) ABSTRACT

The present invention relates in general to methods and products for initiating an immune response against an antigen, and in particular relates to transepithelial delivery of antigens to provoke tolerance and immunity. The present invention further relates to methods and products for the transepithelial delivery of therapeutics. In particular, the invention relates to methods and compositions for the delivery of therapeutics conjugated to a FcRn binding partner to intestinal epithelium, mucosal epithelium and epithelium of the lung. The present invention further relates to the synthesis, preparation and use of the FcRn binding partner conjugates as, or in, pharmaceutical compositions for oral systemic delivery of drugs and vaccines.

28 Claims, 4 Drawing Sheets

OTHER PUBLICATIONS

Elson et al., J Immunol 135:930-932 (1985).
Farges R et al., FEBS Lett 335 (3):305-308 (Oct. 12, 1993).
Fridman WH, FASEB J 5(12):2684-2690 (Sep. 1991).
Fritsche et al., J Allergy Clin Immunol 93:778-786 (1994).
Ghetie V et al., Immunology Today 18(12):592 (Dec. 1997).
Gosselin EJ et al., J Immunol 149:3477-3481 (1992).
Guyer et al., J Immunol 117:587-593 (1976).
Huber et al., Mol Biol 230:1077-1083 (1993).
International Search Report—PCT/US98/15395.
Israel et al., J. Immunol 154(12):6246-6251 (Jun. 15, 1995).
Kobayashi et al., J Immunol 146:68-74 (1991).
Langermann et al., J Exp Med 180:2277-2286 (1994).
Langermann et al., Nature 372:552-555 (1994).
Lencer WI et al., J Cell Biol 117:1197-1209 (1992).
Lencer WI et al., J Clin Invest 92:2941-2951 (1993).
Lund et al., J Immunol 147:2657-2662 (1991).
Mikael N et al., Lupus 3:173-179 (1994).
Mostov et al., Cell 43:389-390 (1985).
Patel et al., FEBS Lett 234(2):321-325 (1988).
Paul WF (ed)., Fundamental Immunology, 4th edition, pp. 1399-1401 (1999).
Rabinovich NR et al., Science 265:1401-1404 (1994).
Raghavan M et al., Immunity 1:303-315 (Jul. 1994).
Service RF, Science 265:1522-1524 (1994).
Simister NE et al., Nature 337:184-187 (1989).
Simister NE, American Society of Microbiology Press, Washington, DC pp. 57-73 (1990).
Squire CM et al., J Immunol 152:4388-4396 (1994).
Story CM et al., J Exp Med 180:2377-2381 (1994).
Supplementary Search Report—EP 96 90 3522.
Woof et al., Mol Immunol 23:319-330 (1986).
Kim JK et al., Localization of the site of the murine IgG1 molecule that is involved in binding to the murine intestinal Fc receptor. *Eur J Immunol*. Oct. 24, 1994;(10):2429-34.

* cited by examiner

```
                                                                                          899
840  gtcgtcgACAAAACTCACACATGCCCACCGTGCCCAGCACCTGAACTCCTGGGGGACCG
     +----+----+----+----+----+----+----+----+----+----+----+----+
     cagcagcTGTTTTGAGTGTGTACGGGTGGCACGGGTCGTGGACTTGAGGACCCCCCTGGC
     S  S  S  T  K  L  T  H  A  H  R  A  Q  H  L  N  S  W  G  D  R  -
        R  R  Q  N  S  H  M  P  T  V  P  S  T  *  T  P  G  G  T  V  -
     V  V  D  K  T  H  T  C  P  P  C  P  A  P  E  L  L  G  G  P    -

959
     TCAGTCTTCCTCTTCCCCCCAAAACCCAAGGACACCCTCATGATCTCCCGGACCCCTGAG
900  +----+----+----+----+----+----+----+----+----+----+----+----+
     AGTCAGAAGGAGAAGGGGGGTTTTGGGTTCCTGTGGGAGTACTAGAGGGCCTGGGGACTC
     Q  S  S  S  P  Q  N  P  R  T  P  S  *  S  P  G  P  L  R    -
        S  L  P  L  P  P  K  T  Q  G  H  P  H  D  L  P  D  P  *  G  -
     S  V  F  F  P  P  K  P  K  D  T  L  M  I  S  R  T  P  E    -

1019
     GTCACATGCGTGGTGGTGGACGTGAGCCACGAAGACCCTGAGGTCAAGTTCAACTGGTAC
960  +----+----+----+----+----+----+----+----+----+----+----+----+
     CAGTGTACGCACCACCACCTGCACTCGGTGCTTCTGGGACTCCAGTTCAAGTTGACCATG
     S  H  A  W  W  W  T  *  A  T  K  T  L  R  S  S  S  T  G  T    -
        H  M  R  G  G  G  R  E  P  R  R  R  P  *  G  Q  V  L  V  R -
     V  T  C  V  V  V  D  V  S  H  E  D  P  E  V  K  F  N  W  Y    -
```

FIG. 1A

```
                                                                GTGGACGGGCGTGGAGGTGCATAATGCCAAGACAAAGCCGGGAGGAGCAGTACAACAGC
                                                           1020 +---------+---------+---------+---------+---------+---------+ 1079
                                                                CACCTGCCGCACCTCCACGTATTACGGTTCTGTTTCGGCCCTCCTCGTCATGTTGTCG

W   T   A   W   R   C   I   M   P   R   Q   S   R   G   R   S   S   T   T   A   -
                                                                G   R   G   G   A   *   C   Q   D   K   A   A   G   G   A   V   Q   Q   H   -
                                                                  V   D   G   V   E   V   H   N   A   K   T   K   P   R   E   E   Q   Y   N   S   -

ACGTACCGTGTGTCAGCGTCCTCACCGTCCTCGACGTCCTGACCAGGACTGGCTGAATGGCAAGGAG
                                                           1080 +---------+---------+---------+---------+---------+---------+ 1139
                                                                TGCATGGCACACCAGTCGCAGGAGTGGCAGGACGTGGTCCTGACCGACTTACCGTTCCTC

R   T   V   W   S   A   S   S   P   S   C   T   R   T   G   *   M   A   R   S   -
                                                                V   P   C   G   Q   R   P   H   R   P   A   P   G   L   A   E   W   Q   G   V   -
                                                                  T   Y   R   V   V   S   V   L   T   V   L   H   Q   D   W   L   N   G   K   E   -

TACAAGTGCAAGGTCTCCAACAAAGCCCTCCCAGCCCCCATCGAGAAACCATCTCCAAA
                                                           1140 +---------+---------+---------+---------+---------+---------+ 1199
                                                                ATGTTCACGTTCCAGAGGTTGTTTCGGGAGGGTCGGGGGTAGCTCTTTTGGTAGAGGTT

T   S   A   R   S   P   T   K   P   S   Q   P   P   S   R   K   P   S   P   K   -
                                                                Q   V   Q   G   L   Q   S   P   P   S   P   H   R   E   N   H   L   Q   S   -
                                                                  Y   K   C   K   V   S   N   K   A   L   P   A   P   I   E   K   T   I   S   K   -
```

FIG. 1B

```
GCCAAAGGGCAGCCCCGAGAACCACAGGTGTACACCCTGCCCCATCCCGGGATGAGCTG
1200 +----+----+----+----+----+----+----+----+----+----+----+----+ 1259
CGGTTTCCCGTCGGGGCTCTTGGTGTCCACATGTGGGACGGGGTAGGGCCCTACTCGAC

P  K  G  S  P  E  N  H  R  C  T  P  C  P  H  P  G  M  S  *  -
       Q  R  A  A  P  R  T  T  G  V  Y  T  L  P  P  S  R  D  E  L -
        A  K  G  Q  P  R  E  P  Q  V  Y  H  P  A  P  I  P  G  *  A  D -
                                                        R  D  E  L -

ACCAAGAACCAGGTCAGCCTGACCTGCCTGGTCAAAGGCTTCTATCCCAGCGACATCGCC
1260 +----+----+----+----+----+----+----+----+----+----+----+----+ 1319
TGGTTCTTGGTCCAGTCGGACTGGACGGACCAGTTTCCGAAGATAGGGTCGCTGTAGCGG

P  R  T  R  S  A  *  P  A  W  S  K  A  S  I  P  A  T  S  P -
       Q  E  P  G  Q  P  D  L  P  G  Q  R  L  L  S  Q  R  H  R  R -
        T  K  N  Q  V  S  L  T  C  L  V  K  G  F  Y  P  S  D  I  A -

GTGGAGTGGGAGAGCAATGGGCAGCCGGAGAACAACTACAAGACCACGCCTCCCGTGTTG
1320 +----+----+----+----+----+----+----+----+----+----+----+----+ 1379
CACCTCACCCTCTCGTTACCCGTCGGCCTCTTGTTGATGTTCTGGTGCGGAGGGCACAAC

W  S  G  R  A  M  G  S  R  T  T  T  R  P  R  L  P  C  W -
       G  V  G  E  Q  W  A  G  E  Q  L  Q  D  H  A  S  R  V  G -
        V  E  W  E  S  N  G  Q  P  E  N  N  Y  K  T  T  P  P  V  L -
```

FIG. 1C

```
       GACTCCGACGGCTCCTCTTCCTCTACAGCAAGCTCACCGTGGACAAGAGACAGGTGGCAG
1380 +---------+---------+---------+---------+---------+---------+ 1439
       CTGAGGCTGCCGAGGAGAAGGAGATGTCGTTCGAGTGGCACCTGTTCTCGTCCACCGTC

T  P  T  A  P  S  S  S  T  A  S  S  P  W  T  R  A  G  G  S  -
      L  R  R  L  L  P  L  Q  Q  A  H  R  G  Q  E  Q  V  A  A  -
     D  S  D  G  S  F  F  L  Y  S  K  L  T  V  D  K  S  R  W  Q  -

CAGGGAACGTCTTCTCATGCTCCGTGATGCATGAGGCTCTGCACAACCACTACACGCAG
1440 +---------+---------+---------+---------+---------+---------+ 1499
       GTCCCCTTGCAGAAGAGTACGAGGCACTACTACGTACTCCGAGACGTGTTGGTGATGTGCGTC

R  G  T  S  S  H  A  P  *  C  M  R  L  C  T  T  T  T  R  R  -
      G  E  R  L  L  M  L  R  D  A  *  G  S  A  Q  P  L  H  A  E  -
     Q  G  N  V  F  S  C  S  V  M  H  E  A  L  H  N  H  Y  T  Q  -

Not
                                                         1

AAGAGCCTCTCCCTGTCTCCGGGTAAATGAGTGCGGGGCCCGgtc
1500 +---------+---------+---------+---------+----- 1545
       TTCTCGGAGAGGGACAGAGGCCCATTTACTCACGCCCCGGGCcag R  A  S  P  C  L  R  V  N  E  C  G  G  R  V
      E  P  L  P  V  S  G  *  M  S  A  A  A  A
     K  S  L  S  L  S  P  G  K  *  V  R  R  P  R
```

FIG. 1D

SEQUENCE LISTING

<160> NUMBER OF SEQ ID NOS: 22

<210> SEQ ID NO 1
<211> LENGTH: 706
<212> TYPE: DNA
<213> ORGANISM: Homo sapiens

<400> SEQUENCE: 1

```
gtcgtcgaca aaactcacac atgcccaccg tgcccagcac ctgaactcct gggggggaccg      60 tcagtcttcc tcttcccccc aaaacccaag gacaccctca tgatctcccg gacccctgag     120
gtcacatgcg tggtggtgga cgtgagccac gaagaccctg aggtcaagtt caactggtac     180
gtggacggcg tggaggtgca taatgccaag acaaagccgc gggaggagca gtacaacagc     240
acgtaccgtg tggtcagcgt cctcaccgtc ctgcaccagg actggctgaa tggcaaggag     300
tacaagtgca aggtctccaa caaagccctc ccagccccca tcgagaaaac catctccaaa     360 gccaagggc agccccgaga accacaggtg tacaccctgc ccccatcccg ggatgagctg     420
accaagaacc aggtcagcct gacctgcctg gtcaaaggct tctatcccag cgacatcgcc     480
gtggagtggg agagcaatgg gcagccggag aacaactaca agaccacgcc tcccgtgttg     540
gactccgacg gctccttctt cctctacagc aagctcaccg tggacaagag caggtggcag     600
caggggaacg tcttctcatg ctccgtgatg catgaggctc tgcacaacca ctacacgcag     660
aagagcctct ccctgtctcc gggtaaatga gtgcggcggc cgcgtc                   706
```

<210> SEQ ID NO 2
<211> LENGTH: 229
<212> TYPE: PRT
<213> ORGANISM: Homo sapiens

<400> SEQUENCE: 2

```
Val Val Asp Lys Thr His Thr Cys Pro Pro Cys Pro Ala Pro Glu Leu
  1               5                  10                  15

Leu Gly Gly Pro Ser Val Phe Leu Phe Pro Pro Lys Pro Lys Asp Thr
             20                  25                  30

Leu Met Ile Ser Arg Thr Pro Glu Val Thr Cys Val Val Val Asp Val
         35                  40                  45
```

```
Ser His Glu Asp Pro Glu Val Lys Phe Asn Trp Tyr Val Asp Gly Val
 50                  55                  60

Glu Val His Asn Ala Lys Thr Lys Pro Arg Glu Gln Tyr Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Ala Leu Pro Ala
                100                 105                 110

Pro Ile Glu Lys Thr Ile Ser Lys Ala Lys Gly Gln Pro Arg Glu Pro
            115                 120                 125

Gln Val Tyr Thr Leu Pro Pro Ser Arg Asp Glu Leu Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
195                 200                 205

Val Met His Glu Ala Leu His Asn His Tyr Thr Gln Lys Ser Leu Ser
    210                 215                 220

Leu Ser Pro Gly Lys
225

<210> SEQ ID NO 3
<211> LENGTH: 5
<212> TYPE: PRT
<213> ORGANISM: Homo sapiens

<400> SEQUENCE: 3

Val Arg Arg Pro Arg
1               5

<210> SEQ ID NO 4
<211> LENGTH: 33
<212> TYPE: PRT
<213> ORGANISM: Homo sapiens

<400> SEQUENCE: 4

Ser Ser Thr Lys Leu Thr His Ala His Arg Ala Gln His Leu Asn Ser
1               5                   10                  15

Trp Gly Asp Arg Gln Ser Ser Ser Pro Gln Asn Pro Arg Thr Pro
            20                  25                  30

Ser

<210> SEQ ID NO 5
<211> LENGTH: 13
<212> TYPE: PRT
<213> ORGANISM: Homo sapiens

<400> SEQUENCE: 5

Ser Pro Gly Pro Leu Arg Ser His Ala Trp Trp Trp Thr
1               5                   10

<210> SEQ ID NO 6
<211> LENGTH: 47
<212> TYPE: PRT
```

<213> ORGANISM: Homo sapiens

<400> SEQUENCE: 6

Ala Thr Lys Thr Leu Arg Ser Ser Thr Gly Thr Trp Thr Ala Trp
1               5                   10                  15

Arg Cys Ile Met Pro Arg Gln Ser Arg Gly Arg Ser Ser Thr Thr Ala
            20                  25                  30

Arg Thr Val Trp Ser Ala Ser Pro Ser Cys Thr Arg Thr Gly
        35                  40                  45

<210> SEQ ID NO 7
<211> LENGTH: 43
<212> TYPE: PRT
<213> ORGANISM: Homo sapiens

<400> SEQUENCE: 7

Met Ala Arg Ser Thr Ser Ala Arg Ser Pro Thr Lys Pro Ser Gln Pro
1               5                   10                  15

Pro Ser Arg Lys Pro Ser Pro Lys Pro Lys Gly Ser Pro Glu Asn His
            20                  25                  30

Arg Cys Thr Pro Cys Pro His Pro Gly Met Ser
        35                  40

<210> SEQ ID NO 8
<211> LENGTH: 6
<212> TYPE: PRT
<213> ORGANISM: Homo sapiens

<400> SEQUENCE: 8

Pro Arg Thr Arg Ser Ala
1               5

<210> SEQ ID NO 9
<211> LENGTH: 61
<212> TYPE: PRT
<213> ORGANISM: Homo sapiens

<400> SEQUENCE: 9

Pro Ala Trp Ser Lys Ala Ser Ile Pro Ala Thr Ser Pro Trp Ser Gly
1               5                   10                  15

Arg Ala Met Gly Ser Arg Arg Thr Thr Thr Arg Pro Arg Leu Pro Cys
            20                  25                  30

Trp Thr Pro Thr Ala Pro Ser Ser Thr Ala Ser Ser Pro Trp Thr
        35                  40                  45

Arg Ala Gly Gly Ser Arg Gly Thr Ser Ser His Ala Pro
    50                  55                  60

<210> SEQ ID NO 10
<211> LENGTH: 26
<212> TYPE: PRT
<213> ORGANISM: Homo sapiens

<400> SEQUENCE: 10

Cys Met Arg Leu Cys Thr Thr Thr Arg Arg Ala Ser Pro Cys
1               5                   10                  15

Leu Arg Val Asn Glu Cys Gly Gly Arg Val
            20                  25

<210> SEQ ID NO 11
<211> LENGTH: 13
<212> TYPE: PRT

```
<213> ORGANISM: Homo sapiens

<400> SEQUENCE: 11

Arg Arg Gln Asn Ser His Met Pro Thr Val Pro Ser Thr
 1               5                  10

<210> SEQ ID NO 12
<211> LENGTH: 24
<212> TYPE: PRT
<213> ORGANISM: Homo sapiens

<400> SEQUENCE: 12

Thr Pro Gly Gly Thr Val Ser Leu Pro Leu Pro Lys Thr Gln Gly
 1               5                  10                  15

His Pro His Asp Leu Pro Asp Pro
             20

<210> SEQ ID NO 13
<211> LENGTH: 13
<212> TYPE: PRT
<213> ORGANISM: Homo sapiens

<400> SEQUENCE: 13

Gly His Met Arg Gly Gly Gly Arg Glu Pro Arg Arg Pro
 1               5                  10

<210> SEQ ID NO 14
<211> LENGTH: 13
<212> TYPE: PRT
<213> ORGANISM: Homo sapiens

<400> SEQUENCE: 14

Gly Gln Val Gln Leu Val Arg Gly Arg Arg Gly Gly Ala
 1               5                  10

<210> SEQ ID NO 15
<211> LENGTH: 70
<212> TYPE: PRT
<213> ORGANISM: Homo sapiens

<400> SEQUENCE: 15

Cys Gln Asp Lys Ala Ala Gly Gly Ala Val Gln Gln His Val Pro Cys
 1               5                  10                  15

Gly Gln Arg Pro His Arg Pro Ala Pro Gly Leu Ala Glu Trp Gln Gly
                 20                  25                  30

Val Gln Val Gln Gly Leu Gln Gln Ser Pro Pro Ser Pro His Arg Glu
             35                  40                  45

Asn His Leu Gln Ser Gln Arg Ala Ala Pro Arg Thr Thr Gly Val His
         50                  55                  60

Pro Ala Pro Ile Pro Gly
65                  70

<210> SEQ ID NO 16
<211> LENGTH: 72
<212> TYPE: PRT
<213> ORGANISM: Homo sapiens

<400> SEQUENCE: 16

Ala Asp Gln Glu Pro Gly Gln Pro Asp Leu Pro Gly Gln Arg Leu Leu
 1               5                  10                  15

Ser Gln Arg His Arg Arg Gly Val Gly Glu Gln Trp Ala Ala Gly Glu
                 20                  25                  30
```

-continued

```
Gln Leu Gln Asp His Ala Ser Arg Val Gly Leu Arg Arg Leu Leu Leu
        35                  40                  45

Pro Leu Gln Gln Ala His Arg Gly Gln Glu Gln Val Ala Ala Gly Glu
    50                  55                  60

Arg Leu Leu Met Leu Arg Asp Ala
65                  70

<210> SEQ ID NO 17
<211> LENGTH: 16
<212> TYPE: PRT
<213> ORGANISM: Homo sapiens

<400> SEQUENCE: 17

Gly Ser Ala Gln Pro Leu His Ala Glu Glu Pro Leu Pro Val Ser Gly
1               5                   10                  15

<210> SEQ ID NO 18
<211> LENGTH: 6
<212> TYPE: PRT
<213> ORGANISM: Homo sapiens

<400> SEQUENCE: 18

Met Ser Ala Ala Ala Ala
1               5

<210> SEQ ID NO 19
<211> LENGTH: 17
<212> TYPE: DNA
<213> ORGANISM: Homo sapiens

<400> SEQUENCE: 19
tgctgggctg tgaactg                                                    17

<210> SEQ ID NO 20
<211> LENGTH: 18
<212> TYPE: DNA
<213> ORGANISM: Homo sapiens

<400> SEQUENCE: 20
cgcttttagc agtcggaa                                                   18

<210> SEQ ID NO 21
<211> LENGTH: 4
<212> TYPE: PRT
<213> ORGANISM: Homo sapiens

<400> SEQUENCE: 21

Asp Lys Thr His
 1

<210> SEQ ID NO 22
<211> LENGTH: 4
<212> TYPE: PRT
<213> ORGANISM: Homo sapiens

<400> SEQUENCE: 22

Ser Pro Gly Lys
 1
```

RECEPTOR SPECIFIC TRANSEPITHELIAL TRANSPORT IN THERAPEUTICS

This is a division of U.S. Ser. No. 09/122,144, filed Jul. 24, 1998 (now U.S. Pat. No. 6,485,726), which is a continuation-in-part of and claims priority to U.S. Ser. No. 08/899,856, filed Jul. 24, 1997 (now U.S. Pat. No. 6,030,613), which is a continuation-in-part of U.S. Ser. No. 08/578,171, filed on Dec. 29, 1995 (abandoned), which is a continuation-in-part of U.S. Ser. No. 08/374,159, filed on Jan. 17, 1995 (now U.S. Pat. No. 6,086,875).

The work described herein was supported, in part, by National Institutes of Health Grant Nos. NIH DK-44319, NIH HO-27691 and NIH DK-48106. The U.S. Government has certain rights to this invention.

1. FIELD OF THE INVENTION

The present invention relates in general to methods and products for initiating an immune response against an antigen, and in particular relates to transepithelial delivery of antigens to provoke tolerance and immunity.

The present invention further relates to methods and products for the transepithelial delivery of therapeutics. In particular, the invention relates to methods and compositions for the delivery of therapeutics conjugated to a FcRn binding partner to intestinal epithelium, mucosal epithelium and epithelium of the lung. The present invention further relates to the synthesis, preparation and use of the FcRn binding partner conjugates as, or in, pharmaceutical compositions for oral systemic delivery of drugs and vaccines.

2. BACKGROUND OF THE INVENTION

The immune system of a mammal develops during gestation and becomes active in the late mammalian fetus. Although active, it still might be characterized as 'immature' because it has not been challenged to any significant extent by antigens; the fetus is largely protected from antigens by the mother. This 'immature' immune system, however, is supplemented by the transfer of maternal immunoglobulin to the fetus (or in some cases to the neonate) to provide humoral immunity during the first weeks of independent life.

Rats and mice receive most maternal immunoglobulin G (IgG) by suckling from colostrum and milk, although some is acquired prenatally. Cattle also receive IgG from colostrum. In rabbits, IgG is transported to the fetus across the yolk sac. Little is know about the transfer of IgG to the fetus or neonate in humans. Most evidence suggests that human mothers transfer humoral immunity to an offspring only before birth, although IgA transferred to a neonate via breast milk is believed to play a role in protecting the neonate against enteric infection.

The delivery of maternal IgG to the mammalian fetus and/or neonate requires transport across an epithelial barrier which is largely impervious to macromolecules. The transport of macromolecules across such an epithelial barrier may occur by non-specific and specific receptor-mediated mechanisms. Receptor non-specific mechanisms are represented by paracellular sieving events, the efficiency of which are inversely related to the molecular weight of the transported molecule. Transport of macromolecules such as IgG across this paracellular pathway is highly inefficient. Descriptions of receptor-mediated transport of immunoglobulins through intestinal epithelial cells are limited thus far to the polymeric immunoglobulin receptor and the enterocyte receptor of IgG (a major histocompatibility complex (MHC) class I related Fc receptor). These two receptor systems differ in their specificity for immunoglobulin isotype, in their direction of immunoglobulin transport across the epithelial cell and in their tissue-specific expression. Both may play a role in molding the immature immune system.

The polymeric immunoglobulin receptor is expressed on the basolateral surfaces of enterocytes, hepatocytes and/or biliary duct epithelial cells. It transports polymeric IgA and IgM to the apical (luminal) surfaces, concentrating these immunoglobulins for antimicrobial defense and antigen exclusion.

The enterocyte receptor for IgG, which has homology to the MHC class I heavy chain and is associated with $beta_2$-microglobulin ($\beta_2M$), is expressed on neonatal enterocytes of the rat and mouse. IgG is transported transcellularly in a luminal to serosal direction across the intestinal epithelium of these rodent neonates. On the apical surface of the enterocyte, the Fc portion of IgG is bound to the enterocyte receptor at the relatively acidic pH of the lumen (about pH 6.0). Following transcytosis to the basolateral plasma membrane, discharge of the immunoglobulin occurs at the relatively neutral pH of the interstitial fluids (about pH 7.4). The rodent neonatal Fc receptor (FcRn) therefore could be responsible for delivery of maternal IgG to the neonate and as such may be responsible for the passive acquisition of IgG during this period.

In humans, maternal IgG is actively transported across the placenta. The receptor responsible for this transport has been sought for many years. Several IgG-binding proteins have been isolated from placenta. FcγRII was detected in placental endothelium and FcγRIII in syncytiotrophoblasts. Both of these receptors, however, showed a relatively low affinity for monomeric IgG. Recently, the isolation from placenta of a cDNA encoding a human homolog of the rat and mouse enterocyte receptor for IgG was reported. (Story, C. M. et al., J. Exp. Med., Vol. 180:2377–2381, December 1994) The complete nucleotide and deduced amino acid sequence is reported. This Fc receptor for IgG may be responsible for the transport of maternal IgG to the human fetus (and even possibly to the neonate), as the molecule is highly homologous over its open reading frame with the rat FcRn sequence (69% nucleotide identity and 65% predicted amino acid identity). So called passive immunization in the human fetus (and possibly in the human neonate) now may become better understood.

In contrast to passive immunization which involves supplementing a host's immune system with antibodies derived from another, active immunization involves stimulation of the host's own immune system to generate in vivo the desired immune response. The most widely practiced methods of active immunization in children and adults involve injections of an immunogen, once as an initial dose and then at least once again as a booster dose. These methods suffer many serious drawbacks, including the risks associated with the use of needles that can transmit diseases such as AIDS and hepatitis. (When tolerizing a patient against an allergen, the problems are compounded in that repeated injections over a long period of time often are required.) These methods also do not necessarily trigger adequately the first line of defense against many pathogens, that is, mucosal immunity. Mucous membranes line the airways, the reproductive system and the gastrointestinal tract, and this mucosal surface represents the first portal of entry for many diseases. An oral vaccine that is easy to deliver and that triggers mucosal immunity would be highly desirable.

Immunization using oral vaccines is problematic. Often little or no immune response is achieved. To enhance the immune response, antigens of interest have been coupled to carriers that are known to be strongly immunogenic. For example, researchers have delivered antigens using Bacille Calmette-Guérin (BCG) as a carrier; BCG is a bacterium originally used as an oral vaccine against tuberculosis. A problem with such carriers is that the patient will develop antibodies against the carrier itself, which can be troublesome if the carrier is used again for delivering a different antigen to the same patient. To date, no general strategy for oral vaccines has proven successful.

Immunoglobulin and portions thereof in the past have been conjugated to drugs and imaging agents to target and destroy cell populations and to extend the half-lives of certain agents. Immunotoxins are an example of such conjugates. Such conjugates, however, have never been proposed as useful for initiating an immune response.

A small body of work has focused on the tolerogenic capacity of immunoglobulins coupled to oligonucleotides or proteins characteristic of autoimmune diseases. (See PCT WO 91/08773). This work is based upon the notion that the induction of tolerance may be strongly influenced by carrier moieties and that immunoglobulin carriers appear to be strongly tolerogenic. Isologous IgG is the preferred carrier, and intravenous administration was the mode used for delivering the conjugates of IgG. Although this body of work extends for more than a decade, oral administration is mentioned only once and only for conjugates where IgA is the immunoglobulin carrier. Thus, although tolerogenic immunoglobulin conjugates are known in the art, such conjugates have never been suggested as agents for inducing a robust response against an antigen characteristic of a pathogen. (To the contrary, the art suggests that such conjugates, if anything, would tolerize a subject against a pathogen which would be highly undesirable). In addition, it never has been suggested that such conjugates would be effective tolerogens when the immunoglobulin is IgG and the mode of delivery is oral delivery.

3. SUMMARY OF THE INVENTION

The invention involves the discovery that antigens may be coupled to molecules that bind to the FcRn receptor, such as immunoglobulins, or portions thereof, and delivered across epithelial barriers by active transport through the enterocyte via FcRn receptors. The immunoglobulin or portion thereof binds to the FcRn receptor and acts as a carrier for the antigen as the immunoglobulin or portion thereof is transported across the epithelial barrier by FcRn mediated-transport. The FcRn receptor is present in the human epithelial tissue of children and adults, and the invention therefore permits effective strategies for immunizing humans.

According to one aspect of the invention, a method for modulating the immune system of a mammal is provided. An effective amount of a conjugate of an antigen and a FcRn binding partner is administered to an epithelial barrier of a mammal in need of such immune modulation. The antigen is selected from the group consisting of: an antigen that is characteristic of a pathogen, an antigen that is characteristic of an autoimmune disease, an antigen that is characteristic of an allergen and an antigen that is characteristic of a tumor.

The FcRn binding partners of the present invention may be utilized for the delivery of a wide variety of compounds and therapeutics and bioactive substances, including but not limited to, chemotherapy agents for the treatment of cancer, cytokines, including interferon; and hormones including insulin, human growth hormone (HGH), fertility drugs, calcitonin, calcitriol and other bioactive steroids. The FcRn binding partners of the present invention may further be utilized for the targeted delivery of a delivery vehicle, such as liposomes.

In preferred embodiments, the FcRn binding partner is non-specific IgG or a FcRn binding fragment of IgG. Most preferably the FcRn binding partner is an Fc fragment of IgG. It also is preferred that the antigen be covalently coupled to the FcRn binding partner. Preferably the conjugate is administered orally to the intestinal epithelium, in an aerosol to the lungs or intranasally. Such preparations may be nonaseptic. Supplementary potentiating agents, as described below, may be administered in addition.

In a preferred embodiment, when the compound to be delivered is a peptide or protein, the FcRn binding partner protein conjugate may be synthesized as a recombinant fusion protein. Examples of peptides and proteins which may be conjugated in this manner include cytokines; chemokines; growth factors, insulin, erythropoietin (EPO), neuropeptides, neuropeptide Y, neurotensin, transforming growth factor α, transforming growth factor β, interferon (IFN), and hormones.

The pharmaceutical compositions of the present invention relate to FcRn binding partners conjugated to bioactive substances, including vaccines or drugs for oral, sublingual or intranasal systemic delivery. The pharmaceutical preparation of the present invention includes a conjugate of an antigen and a FcRn binding partner, wherein the antigen is selected from the group consisting of: an antigen that is characteristic of a pathogen, an antigen that is characteristic of an autoimmune disease, an antigen that is characteristic of an allergen and an antigen that is characteristic of a tumor. The pharmaceutical preparation of the present invention includes a conjugate of a drug or therapeutic and a FcRn binding partner. The preferred-FcRn binding partners are as described above. The conjugate is present in an amount effective for modulating the immune response of a mammal. The pharmaceutical preparation of the present invention also includes a pharmaceutically acceptable carrier. When the antigen is characteristic of an autoimmune disease or an allergen, then the pharmaceutical preparations of the invention must be formulated in unit dosage form constructed and arranged for delivery to an epithelial barrier such as for oral delivery to the intestinal epithelium, aerosol delivery to the pulmonary epithelium and intranasal delivery to the nasal epithelium. Thus tablets containing IgG (or an FcRn binding portion thereof) coupled to any of the antigens as characterized above are embraced by the present invention.

The foregoing pharmaceutical preparations may be delivered together with supplementary potentiating agents including adjuvants, cytokines, bioadhesives and the like. The supplementary potentiating agents themselves may be coupled to a FcRn binding partner to facilitate the delivery of such agents across the epithelial barrier. Preferred modes of administration in general include oral dosages to the intestinal epithelium, aerosols to the lungs and intranasal dosages.

The present invention further relates to the synthesis, preparation and use of the FcRn binding partner conjugates of the present invention as, or in, pharmaceutical compositions for oral and intranasal systemic delivery of drugs and vaccines. The synthesis of the FcRn binding partner conjugates of the present invention comprises covalently coupling an antigen or a supplementary potentiating agent to an FcRn binding partner, wherein the antigen or supplementary potentiating agent is selected as described above. The synthesis of the FcRn binding partner conjugates of the present invention alternatively comprises covalently coupling a FcRn binding partner to a therapeutic or drug. Further, the synthesis of the FcRn binding partner conjugates of the present invention comprise covalently coupling a FcRn binding partner to a delivery vehicle, e.g. liposomes. The preferred FcRn binding partner also is as described above. The conjugates then can be used to prepare the pharmaceutical preparations of the present invention.

In yet another aspect of the invention, the conjugate including the antigen crosses the epithelial barrier in an amount at least double the extent that the antigen crosses the epithelial barrier in an unconjugated form. It thus is an object of the invention to develop a mechanism for increasing the ability of an antigen to cross an epithelial barrier.

Another object of the invention is to develop a new class of orally active immunogens and toleragens.

Another object of the invention is to develop improved methods for stimulating mucosal immunity.

These and other aspects of the invention are described in greater detail below.

4. BRIEF DESCRIPTION OF DRAWING

FIG. 1. Nucleotide and Amino Acid Sequence of Fc fragment of human IgG.

5. DETAILED DESCRIPTION OF THE INVENTION

The present invention relates to FcRn binding partners modified for the targeted delivery of vaccines, antigens, drugs, therapeutics and liposomes to epithelial barriers. The invention involves the discovery that the human FcRn receptor is active in adult epithelial tissue and the discovery that FcRn binding partners such as IgG or Fc fragments can be used to transport other molecules, including antigens, across epithelial barriers. In this manner, "FcRn binding partners", such as IgG or an FcRn binding portion thereof can be used to deliver an antigen or a therapeutic across an epithelial barrier to systemic circulation thereby eliciting a beneficial response or effect, e.g., an immune response.

The invention is useful whenever it is desirable to enhance the delivery of an antigen across an epithelial barrier to the immune system. The invention thus may be used to deliver antigens across intestinal epithelial tissue, lung epithelial tissue and other mucosal surfaces including nasal surfaces, vaginal surfaces, colon surfaces and biliary tree surfaces. The invention may be used to modulate a subjects s immune system such as by stimulating a humoral antibody response against an antigen, by stimulating T cell activity, or by stimulating tolerance to an antigen. As used herein, subject means: humans, primates, horses, cows, sheep, pigs, goats, dogs, cats, chickens and rodents. When delivering, tumor antigens, the invention may be used to treat subjects having disease amenable to immunity mediated rejection, such as non-solid tumors or solid tumors of small size. It is also contemplated that delivery of tumor antigens by the methods described herein will be useful for treatment subsequent to removal of large solid tumors. The invention may also be used to treat subjects who are suspected of having cancer.

The invention is also useful whenever it is desirable to achieve systemic delivery of a therapeutic or drug or delivery vehicle or protein or combinations thereof, across an epithelial barrier to systemic circulation. The invention, thus may be used to deliver therapeutics across intestinal epithelial tissue, lung epithelial tissue, and other mucosal epithelial surfaces including nasal surfaces, vaginal surfaces, colon and rectal surfaces and biliary tree surfaces. The invention may be used to administer a therapeutic to elicit a beneficial effect. The FcRn binding partner conjugates are designed to deliver a wide variety of therapeutics including RNA and DNA nucleotides as used, for example, in gene therapy, peptides, carbohydrates and small molecules. These therapeutics include but are not limited to, anticancer and chemotherapeutic drugs, e.g., doxorubicin; anti-inflammatory drugs, e.g., steroids; drugs for the treatment of cardiovascular disease, e.g., cholinesterase inhibitors; drugs for the treatment of disorders related to viral infection, e.g. hepatic cirrhosis resulting from hepatitis infection; drugs for the treatment of weight disorders, e.g., amphetamines; antibacterial agents, antifungal agents, cytokines, fertility drugs, antibiotics, hormones, steroids, etc.

The invention involves the formation of a conjugate of an FcRn binding partner and an antigen or a therapeutic or drug. By conjugate it is meant two or more entities bound to one another by any physiochemical means, including, but not limited to, hydrophobic interaction, covalent interaction, hydrogen bond interaction, or ionic interaction between a bioactive substance, such as, an antigen or a therapeutic and the non-specific hydrophobic portions of an antibody molecule, antibody-antigen specific binding and covalent coupling. The nature of the preferred bonding will depend, among other things, upon the mode of administration and the pharmaceutical carriers used to deliver the conjugate to the selected epithelial barrier. For example, some bonds are not as well suited as others to withstand certain environments such as the stomach, but can be protected therefrom by delivery systems which bypass the stomach. It, of course, is important that the bond between the FcRn binding partner and the antigen be of such a nature that it does not destroy the ability of the FcRn binding partner to bind to the FcRn receptor. Such bonds are well known to those of ordinary skill in the art examples are provided in greater detail below. The conjugate further may be formed as a fusion protein, also discussed in greater detail below.

5.1. FcRn Binding Partners

An FcRn binding partner means any entity that can be specifically bound by the FcRn receptor with consequent active transport by the FcRn receptor of the FcRn binding partner. As mentioned above, the FcRn receptor has been isolated for several mammalian species, including humans. The sequence of the human FcRn, rat FcRn and mouse FcRn may be found in Story, C. M. et al, J. Exp. Med., vol. 180:2377–2381, December 1994. The FcRn receptor molecule now is well characterized. The FcRn receptor binds IgG (but not other immunoglobulin classes such as IgA, IgD, IgM and IgE) at a relatively lower pH, actively transports the IgG transcellularly in a luminal to serosal direction, and then releases the IgG at a relatively higher pH found in the interstitial fluids. As will be recognized by those of ordinary skill in the art, FcRn receptors can be isolated by cloning or by affinity purification using, for example, monoclonal antibodies. Such isolated FcRn receptors then can be used to identify and isolate FcRn binding partners, as described below.

FcRn binding partners of the present invention encompass any entity that can be specifically bound by the FcRn receptor, including whole IgG, the Fc fragment of IgG and other fragments of IgG that include the complete binding region for the FcRn receptor. The region of the Fc portion of IgG that binds to the FcRn receptor has been described based upon X-ray crystallography (Burmeister, W. P. et al., Nature, 1994; 372:379–383). The major contact area of Fc with the FcRn receptor is near the junction of the $C_H2$ and $C_H3$ domains. Potential contacts are residues 248, 250–257, 272, 285, 288, 290–291, 308–311 and 314 in $C_H2$ and 385–387, 428 and 433–436 in $C_H3$. (These sites are distinct from those identified by subclass comparison or by site-directed mutagenesis as important for Fc binding to leukocyte FcγRI and Fc-γRII.) The foregoing Fc-FcRn contacts are all within a single Ig heavy chain. It has been noted previously that two FcRn receptors can bind a single Fc molecule. The crystallographic data suggest that in such a complex, each FcRn molecule binds a single polypeptide of the Fc homodimer.

In an embodiment of the present invention, FcRn binding partners other than whole IgG may be used to transport therapeutics across the epithelial barrier. In such an embodiment, it is preferred that a FcRn binding partner is chosen which binds the FcRn with higher affinity than whole IgG. Such a FcRn binding partner has utility in utilizing the FcRn to achieve active transport of a conjugated therapeutic across the epithelial barrier, and also has utility to prevent the binding and transport of whole IgG across the epithelial barrier via the FcRn. The FcRn binding activity of these higher affinity FcRn binding partners may be measured using standard assays known to those skilled in the art, including: (a) transport assays using polarized cells that naturally express the FcRn, or have been genetically engineered to express the FcRn or the alpha chain of the FcRn; (b) protein:protein binding assays using soluble FcRn or fragments thereof, or immobilized FcRn; (c) binding assays utilizing polarized or non-polarized cells that naturally express the FcRn, or have been genetically engineered to express the FcRn or the alpha chain of the FcRn.

5.1.1. Recombinant Synthesis of FcRn Binding Partners

In accordance with the present invention, the FcRn binding partner may be produced by recombinant genetic engineering techniques. Within the scope of the invention are nucleotide sequences encoding human FcRn binding partners. The FcRn binding partners include whole IgG, the Fc fragment of IgG and other fragments of IgG that include the complete binding region for the FcRn. The major contact sites include amino acid residues 248, 250–257, 272, 285, 288, 290–291, 308–311 and 314 of the $C_H2$ and amino acid residues 385–387, 428 and 433–436 of the $C_H3$. Therefore in a preferred embodiment of the present invention are nucleotide sequences encoding regions of the IgG Fc spanning these amino acid residues.

Given the foregoing information, those of ordinary skill in the art will readily recognize that the Fc region of IgG can be modified according to well-recognized procedures such as site-directed mutagenesis and the like to yield modified IgG or modified Fc fragments or portions thereof that will be bound by the FcRn receptor. Such modifications include modifications remote from the FcRn contact sites as well as modifications within the contact sites that preserve or even enhance binding. In addition, other binding partners can be identified and isolated. Antibodies or portions thereof specific for the FcRn receptor and capable of being transported by FcRn once bound can be identified and isolated using well established techniques. Likewise, randomly generated molecularly diverse libraries can be screened and molecules that are bound and transported by FcRn receptors can be isolated using conventional techniques. It is not intended that the invention be limited by the selection of any particular FcRn binding partner.

If the peptide is composed entirely of gene-encoded amino acids, or a portion of it is so composed, the peptide or the relevant portion may also be synthesized using conventional recombinant genetic engineering techniques.

For recombinant production, a polynucleotide sequence encoding the FcRn binding partner is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Maniatis et al., 1989, Molecular Cloning A Laboratory Manual, Cold Spring Harbor Laboratory, N.Y.; and Ausubel et al., 1989, Current Protocols in Molecular Biology, Greene Publishing Associates and Wiley Interscience, N.Y.).

To increase efficiency of production, the polynucleotide can be designed to encode multiple units of the FcRn binding partner separated by enzymatic cleavage sites. The resulting polypeptide can be cleaved (e.g., by treatment with the appropriate enzyme) in order to recover the peptide units. This can increase the yield of peptides driven by a single promoter. When used in appropriate viral expression systems, the translation of each peptide encoded by the mRNA is directed internally in the transcript; e.g., by an internal ribosome entry site, IRES. Thus, the polycistronic construct directs the transcription of a single, large polycistronic mRNA which, in turn, directs the translation of multiple, individual peptides. This approach eliminates the production and enzymatic processing of polyproteins and may significantly increase yield of peptide driven by a single promoter.

A variety of host-expression vector systems may be utilized to express the FcRn binding partners described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding linear or non-cyclized forms of the cyclic peptides of the invention may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843) or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. For reviews of such techniques see, e.g., Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9.

In one insect expression system that may be used to produce the peptides of the invention, *Autographa californica* nuclear polyhidrosis virus (AcNPV) is used as a vector to express the foreign genes. The virus grows in *Spodoptera frugiperda* cells. A coding sequence may be cloned into non-essential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., 1983, J. Virol. 46:584; Smith, U.S. Pat. No. 4,215,051). Further examples of this expression system may be found in Current Protocols in Molecular Biology, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, Proc. Natl. Acad. Sci. (USA) 81:3655–3659). Alternatively, the vaccinia 7.5 K promoter may be used, (see, e.g., Mackett et al., 1982, Proc. Natl. Acad. Sci. (USA) 79:7415–7419; Mackett et al., 1984, J. Virol. 49:857–864; Panicali et al., 1982, Proc. Natl. Acad. Sci. 79:4927–4931).

5.2. FcRn Binding Partners Conjugated to Antigens for Vaccine Delivery

The FcRn binding partner is conjugated with an antigen. An antigen as used herein falls into four classes: 1) antigens that are characteristic of a pathogen; 2) antigens that are characteristic of an autoimmune disease; 3) antigens that are characteristic of an allergen; and 4) antigens that are characteristic of a tumor. Antigens in general include polysaccharides, glycolipids, glycoproteins, peptides, proteins, carbohydrates and lipids from cell surfaces, cytoplasm, nuclei, mitochondria and the like.

Antigens that are characteristic of pathogens include antigens derived from viruses, bacteria, parasites or fungi. Examples of important pathogens include vibrio choleras, enterotoxigenic *Escherichia coli*, rotavirus, *Clostridium difficile*, *Shigella* species, *Salmonella typhi*, parainfluenza virus, influenza virus, *Streptococcus pneumoniae*, *Borrelia burgdorferi*, HIV, *Streptococcus mutans*, *Plasmodium falciparum*, *Staphylococcus aureus*, rabies virus and Epstein-Barr virus.

Viruses in general include but are not limited to those in the following families: picornaviridae; caliciviridae; togaviridae; flaviviridae; coronaviridae; rhabdoviridae; filoviridae; paramyxoviridae; orthomyxoviridae; bunyaviridae; arenaviridae; reoviridae; retroviridae; hepadnaviridae; parvoviridae; papovaviridae; adenoviridae; herpesviridae; and poxyviridae.

Bacteria in general include but are not limited to: *P. aeruginosa*; *E. coli*, *Klebsiella* sp.; *Serratia* sp.; *Pseudomonas* sp.; *P. cepacia*; *Acinetobacter* sp.; *S. epidermidis*; *E. faecalis*; *S. pneumoniae*; *S. aureus*; *Haemophilus* sp.; *Neisseria* Sp.; *N. meningitidis*; *Bacteroides* sp.; *Citrobacter* sp.; *Branhamella* sp.; *Salmonella* sp.; *Shigella* sp.; *S. pyogenes*; *Proteus* sp.; *Clostridium* sp.; *Erysipelothrix* sp.; *Listeria* sp.; *Pasteurella multocida*; *Streptobacillus* sp.; *Spirillum* sp.; *Fusospirocheta* sp.; *Treponema pallidum*; *Borrelia* sp.; *Actinomycetes*; *Mycoplasma* sp.; *Chlamydia* sp.; *Rickettsia* sp.; *Spirochaeta*; *Legionella* sp.; *Mycobacteria* sp.; *Ureaplasma* sp.; *Streptomyces* sp.; *Trichomonas* sp.; and *P. mirabilis*.

Parasites include but are not limited to: *Plasmodium falciparum*, *P. vivax*, *P. ovale*, *P. malaria*; *Toxoplasma gondii*; *Leishmania mexicana*, *L. tropica*, *L. major*, *L. aethiopia*, *L. donovani*, *Trypanosoma cruzi*, *T. brucei*, *Schistosoma mansoni*, *S. haematobium*, *S. japonicum*; *Trichinella spiralis*; *Wuchereria bancrofti*; *Brugia malayi*; *Entamoeba histolytica*; *Enterobius vermicularis*; *Taenia solium*, *T. saginata*, *Trichomonas vaginatis*, *T. hominis*, *T. tenax*; *Giardia lamblia*; *Cryptosporidium parvum*; *Pneumocytis carinii*, *Babesia bovis*, *B. divergens*, *B. microti*, *Isospora belli*, *L hominis*; *Dientamoeba fragilis*; *Onchocerca volvulus*; *Ascaris lumbricoides*; *Necator americanis*; *Ancylostoma duodenale*; *Strongyloides stercoralis*; *Capillaria philippinensis*; *Angiostrongylus cantonensis*; *Hymenolepis nana*; *Diphyllobothrium latum*; *Echinococcus granulosus*, *E. multilocularis*; *Paragonimus westermani*, *P. caliensis*; *Chlonorchis sinensis*; *Opisthorchis felineas*, *G. viverini*, *Fasciola hepatica Sarcoptes scabiei*, *Pediculus humanus*; *Phthirius pubis*; and *Dermatobia hominis*.

Fungi in general include but are not limited to: *Cryptococcus neoformans*; *Blastomyces dermatitidis*; *Aiellomyces dermatitidis*; *Histoplasma capsulatum*; *Coccidioides immitis*; *Candida* species, including *C. albicans*, *C. tropicalis*, *C. parapsilosis*, *C. guilliermondii* and *C. krusei*, *Aspergillus* species, including *A. fumigatus*, *A. flavus* and *A. niger*, *Rhizopus* species; *Rhizomucor* species; *Cunninghammella* species; *Apophysomyces* species, including *A. saksenaea*, *A.*

*mucor* and *A. absidia; Sporothrix schenckii, Paracoccidioides brasiliensis; Pseudallescheria boydii, Torulopsis glabrata;* and *Dermatophytes* species.

Antigens that are characteristic of autoimmune disease typically will be derived from the cell surface, cytoplasm, nucleus, mitochondria and the like of mammalian tissues. Examples include antigens characteristic of uveitis (e.g. S antigen), diabetes mellitus, multiple sclerosis, systemic lupus erythematosus, Hashimoto's thyroiditis, myasthenia gravis, primary myxoedema, thyrotoxicosis, rheumatoid arthritis, pernicious anemia, Addison's disease, scleroderma, autoimmune atrophic gastritis, premature menopause (few cases), male infertility (few cases), juvenile diabetes, Goodpasture's syndrome, pemphigus vulgaris, pemphigoid, sympathetic ophthalmia, phacogenic uveitis, autoimmune haemolytic anemia, idiopathic thrombocytopenic purpura, idiopathic leucopenia, primary biliary cirrhosis (few cases), ulcerative colitis, Sjogren's syndrome, Wegener's granulomatosis, poly/dermatomyositis, and discoid lupus erythematosus.

Antigens that are allergens are generally proteins or glycoproteins, although allergens may also be low molecular weight allergenic haptens that induce allergy after covalently combining with a protein carrier (Remington's Pharmaceutical Sciences). Allergens include antigens derived from pollens, dust, molds, spores, dander, insects and foods. Specific examples include the urushiols (pentadecylcatechol or heptadecylcatechol) of Toxicodendron species such as poison ivy, poison oak and poison sumac, and the sesquiterpenoid lactones of ragweed and related plants.

Antigens that are characteristic of tumor antigens typically will be derived from the cell surface, cytoplasm, nucleus, organelles and the like of cells of tumor tissue. Examples include antigens characteristic of tumor proteins, including proteins encoded by mutated oncogenes; viral proteins associated with tumors; and tumor mucins and glycolipids. Tumors include, but are not limited to, those from the following sites of cancer and types of cancer: lip, nasopharynx, pharynx and oral cavity, esophagus, stomach, colon, rectum, liver, gall bladder, biliary tree, pancreas, larynx, lung and bronchus, melanoma of skin, breast, cervix, uteri, uterus, ovary, bladder, kidney, brain and other parts of the nervous system, thyroid, prostate, testes, Hodgkin's disease, non-Hodgkin's lymphoma, multiple myeloma and leukemia. Viral proteins associated with tumors would be those from the classes of viruses noted above. Antigens characteristic of tumors may be proteins not usually expressed by a tumor precursor cell, or may be a protein which is normally expressed in a tumor precursor cell, but having a mutation characteristic of a tumor. An antigen characteristic of a tumor may be a mutant variant of the normal protein—having an altered activity or subcellular distribution. Mutations of genes giving rise to tumor antigens, in addition to those specified above, may be in the coding region, 5' or 3' noncoding regions, or introns of a gene, and may be the result of point mutations frameshifts, deletions, additions, duplications, chromosomal rearrangements and the like. One of ordinary skill in the art is familiar with the broad variety of alterations to normal gene structure and expression which gives rise to tumor antigens. Specific examples of tumor antigens include: proteins such as Ig-idiotype of B cell lymphoma, mutant cyclin-dependent kinase 4 of melanoma, Pmel-17 (gp 100) of melanoma, MART-1 (Melan-A) of melanoma, p15 protein of melanoma, tyrosinase of melanoma, MAGE 1, 2 and 3 of melanoma, thyroid medullary, small cell lung cancer, colon and/or bronchial squamous cell cancer, BAGE of bladder, melanoma, breast, and squamous-cell carcinoma, gp75 of melanoma, oncofetal antigen of melanoma; carbohydrate/lipids such as muci mucin of breast, pancreas, and ovarian cancer, GM2 and GD2 gangliosides of melanoma; oncogenes such as mutant p53 of carcinoma, mutant ras of colon cancer and HER2/neu proto-oncogene of breast carcinoma; viral products such as human papilloma virus proteins of squamous cell cancers of cervix and esophagus. It is also contemplated that proteinaceous tumor antigens may be presented by HLA molecules as specific peptides derived from the whole protein. Metabolic processing of proteins to yield antigenic peptides is well known in the art; for example see U.S. Pat. No. 5,342,774 (Boon et al.). The present method thus encompasses delivery of antigenic peptides and such peptides in a larger polypeptide or whole protein which give rise to antigenic peptides. Delivery of antigenic peptides or proteins may give rise to humoral or cellular immunity.

Generally, subjects can receive an effective amount of the tumor antigen, and/or peptide derived therefrom by one or more of the methods detailed below. Initial doses can be followed by booster doses, following immunization protocols standard in the art. Delivery of tumor antigens thus may stimulate proliferation of cytolytic T lymphocytes.

In the cases of protein and peptide antigens, covalent linking to an FcRn partner is intended to include linkage by peptide bonds in a single polypeptide chain. Established methods (Sambrook et al., *Molecular Cloning: A Laboratory* Manual. Cold Spring Harbor Press, Cold Spring Harbor, N.Y. 1989) would be used to engineer DNA encoding a fusion protein comprised of the antigenic peptide or protein and an FcRn partner. This DNA would be placed in an expression vector and introduced into bacterial or eukaryotic cells by established methods. The fusion protein would be purified from the cells or from the culture medium by established methods.

In accordance with the present invention, a conjugate may be formed as a fusion protein. Conjugates include fusions of the FcRn binding partner to a protein, peptide or protein derivative such as those listed herein including, but not limited to, antigens, allergens, pathogens or to other proteins or protein derivatives of potential therapeutic interest such as growth factors, colony stimulating factors, growth inhibitory factors, signaling molecules, hormones, steroids, neurotransmitters, or morphogens that would be of use when delivered across an epithelial barrier.

By way of example, but not limitation, proteins used in fusion proteins to synthesize conjugates may include Platelet Derived Growth Factor (PDGF) (U.S. Pat. No. 4,766,073), Platelet Derived Endothelial Cell Growth Factor (PD-ECGF) (U.S. Pat. No. 5,227,302), Human pituitary Growth Hormone (HGH) (U.S. Pat. No. 3,853,833), Transforming Growth Factor Beta (TGFβ) (U.S. Pat. No. 5,168,051), Transforming Growth Factor Alpha (TGFα) (U.S. Pat. No. 5,633,147), Keratinocyte Growth Factor (KGF) (U.S. Pat. No. 5,731,170), Insulin-like Growth Factor I (IGF-I) (U.S. Pat. No. 4,963,665), Epidermal Growth Factor (EGF) (U.S. Pat. No. 5,096,825), Erythropoietin (EPO) (U.S. Pat. No. 4,703,008), Granulocyte-Macrophage Colony Stimulating Factor (GM-CSF) (U.S. Pat. No. 5,200,327), M-CSF (U.S. Pat. No. 5,171,675), Colony Stimulating Factor-1 (CSF-1) (U.S. Pat. No. 4,847,201), Steel factor, Calcitonin, AP-1 proteins (U.S. Pat. No. 5,238,839), Brain Derived Neurotrophic Factor (BDNF) (U.S. Pat. No. 5,229,500). All of the references cited above are incorporated herein by reference in their entirety.

In one embodiment, fusion proteins of the present invention are constructed in which the conjugate consists of an Fc fragment (starting with the amino acids D-K-T-H at the N-terminus of the CH1 region, including the hinge and CH2 regions, and continuing through the S-P-G-K sequence in CH3 region) fused to one of the above listed proteins. As an example, the nucleotide sequences encoding Erythropoietin (EPO) are fused to the Fc binding partner.

In order to engineer the DNA vector encoding the fusion protein FcRn binding partner conjugate, the mammalian expression vector scFvE-sec (described in Persic, et.al. GENE 187:1–8 1997 and incorporated herein by reference in its entirety) was linearized with BssH2 and Not1 and the linearized plasmid was gel purified by protocols standard in the art.

The DNA encoding the protein to be fused to the Fc was prepared as follows. The entire (mouse) EPO sequence was removed from the expression vector (described in Bill et al., Biochem. Biophy. Acta 1261:35–43, 1995, incorporated herein by reference in its entirety) by the restriction enzymes BamHI and SalI sites outside the EPO insert. The linearized fragment was gel purified and modified by standard PCR (Polymerase Chain Reaction) protocols and a BssH2 site added adjacent to the DNA encoding the first N-terminal alanine of mouse EPO (5' end); the DNA encoding the C-terminal end of mouse EPO was modified with a sequence corresponding to an ala-ala-ala linker followed by a SalI restriction site (3' end). The EPO fragment was then cut with BssHI and SalI and gel purified by standard protocols in the art. The Fc fragment was cut with restriction enzymes of SalI and NotI and gel purified.

The three linearized and gel purified DNAs described above, including the scfve-sec vector, Fc fragment and modified EPO DNAs were ligated into a single circular vector by a triple ligation using standard protocols in the art.

It is noted that the DNA encoding EPO may be replaced with DNA encoding any of the above proteins or other proteins of interest or protein fragments thereof by standard techniques to create an Fc fusion protein leading to a conjugate. Similarly this invention allows for the replacement of DNA encoding the Fc fragment in the vector with DNA encoding a FcRn binding partner as described herein. Additionally, this invention allows for the replacement of both the DNA encoding EPO and the DNA encoding the Fc fragment such that the final vector results in a conjugate that associates with the FcRn.

In order to demonstrate that a conjugate made by the fusion of a FcRn binding partner and a protein of interest is capable of retaining biological activity, the example protein above was expressed and assayed for biological activity of erythropoietin in the following manner. The mammalian expression vector containing the EPO-Fc fusion was transfected into CHO (Chinese Hamster Ovary) cells and expressed by standard protocols in the art. Supernatants of transfected or non-transfected CHO cells were collected and injected subcutaneously into Balbc mice. Reticulocyte counts of mice were obtained by coulter FACs analysis by techniques known in the field of the art. Results demonstrated that mice injected with the supernatants of the transfected cells had reticulocyte (mature erythrocytes) counts several fold higher than mice injected with control (untransfected supernatants). Since EPO has been documented to stimulate the production of erythrocytes, the results disclosed herein support the ability of the invention to synthesize biologically active FcRn binding partner conjugates.

Similarly, fusion proteins substituting the Fc fragment for an alternate FcRn binding partner domain in the vector described above would be expected to retain biological activity.

5.3. FcRn Binding Partners Conjugated to Therapeutics for Systemic Drug Delivery The FcRn binding partners may be conjugated to a variety of therapeutics or drugs for targeted systemic delivery. The present invention encompasses the targeted systemic delivery of biologically active substances.

As used herein, the term "biologically active substance" refers to eukaryotic and procaryotic cells, viruses, vectors, proteins, peptides, nucleic acids, polysaccharides and carbohydrates, lipids, glycoproteins, and combinations thereof, and synthetic organic and inorganic drugs exerting a biological effect when administered to an animal. For ease of reference, the term is also used to include detectable compounds such as radiopaque compounds including air and barium, magnetic compounds. The active substance can be soluble or insoluble in water. Examples of biologically active substances include anti-angiogenesis factors, antibodies, growth factors hormones, enzymes, and drugs such as steroids, anti-cancer drugs or antibiotics.

In diagnostic embodiments, the FcRn binding partners may also be conjugated to a pharmaceutically acceptable gamma-emitting moiety, including but not limited to, indium and technetium, magnetic particles, radiopaque materials such as air or barium and fluorescent compounds.

By way of example, and not be limitation, the following classes of drugs may be conjugated to FcRn binding partners for the purposes of delivery to epithelial borders:

Antineoplastic Compounds. Nitrosoureas, e.g., carmustine, lomustine, semustine, strepzotocin; Methylhydrazines, e.g., procarbazine, dacarbazine; steroid hormones, e.g., glucocorticoids, estrogens, progestins, androgens, tetrahydrodesoxycaricosterone, cytokines and growth factors; Asparaginase.

Immunoactive Compounds. Immunosuppressives, e.g., pyrimethamine, trimethopterin, penicillamine, cyclosporine, azathioprine; immunostimulants, e.g., levamisole, diethyl dithiocarbamate, enkephalins, endorphins.

Antimicrobial Compounds. Antibiotics, e.g., β lactam, penicillin, cephalosporins, carbapenims and monobactams, β-lactamase inhibitors, aminoglycosides, macrolides, tetracyclins, spectinomycin; Antimalarials, Amebicides, Antiprotazoal, Antifungals, e.g., amphotericin β, Antiviral, e.g., acyclovir, idoxuridine, ribavirin, trifluridine, vidarbine, gancyclovir.

Parasiticides. Antihalmintics, Radiopharmaceutics, gastrointestinal drugs.

Hematologic Compounds. Immunoglobulins; blood clotting proteins; e.g., antihemophilic factor, factor IX complex; anticoagulants, e.g., dicumarol, heparin Na; fibrolysin inhibitors, tranexamic acid.

Cardiovascular Drugs. Peripheral antiadrenergic drugs, centrally acting antihypertensive drugs, e.g., methyldopa, methyldopa HCl; antihypertensive direct vasodilators, e.g., diazoxide, hydralazine HCl; drugs affecting renin-angiotensin system; peripheral vasodilators, phentolamine; antianginal drugs; cardiac glycosides; inodilators; e.g., amrinone, milrinone, enoximone, fenoximone, imazodan, sulmazole; antidysrhythmic; calcium entry blockers; drugs affecting blood lipids; ranitidine, bosentan, rezulin.

Respiratory Drugs. Sypathomimetic drugs: albuterol, bitolterol mesylate, dobutamine HCl, dopamine HCl, ephedrine SO, epinephrine, fenfluramine HCl, isoproterenol HCl, methoxamine HCl, norepinephrine bitartrate, phenylephrine HCl, ritodrine HCl; cholinomimetic drugs, e.g., acetylcholine Cl; anticholinesterases, e.g., edrophonium Cl; cholinesterase reactivators; adrenergic blocking drugs, e.g., acebutolol HCl, atenolol, esmolol HCl, labetalol HCl, metoprolol, nadolol, phentolamine mesylate, propanolol HCl; antimuscarinic drugs, e.g., anisotropine methylbromide, atropine SO4, clinidium Br, glycopyrrolate, ipratropium Br, scopolamine HBr.

Neuromuscular Blocking Drugs. Depolarizing, e.g., atracurium besylate, hexafluorenium Br, metocurine iodide, succinylcholine Cl, tubocurarine Cl, vecuronium Br; centrally acting muscle relaxants, e.g., baclofen.

Neurotransmitters and neurotransmitter Agents. Acetylcholine, adenosine, adenosine triphosphate, amino acid neurotransmitters, e.g., excitatory amino acids, GABA, glycine; biogenic amine neurotransmitters, e.g., dopamine, epinephrine, histamine, norepinephrine, octopamine, serotonin, tyramine; neuropeptides, nitric oxide, K+ channel toxins, Antiparkinson Drugs. amaltidine HCl, benztropine mesylate, e.g., carbidopa.

Diuretic Drugs. Dichlorphenamide, methazolamide, bendroflumethiazide, polythiazide.

Uterine, Antimigraine Drugs. Carboprost tromethamine, mesylate, methysergide maleate.

Hormones. Pituitary hormones, e.g., chorionic gonadotropin, cosyntropin, menotropins, somatotropin, iorticotropin, protirelin, thyrotropin, vasopressin, lypressin; adrenal hormones, e.g., beclomethasone dipropionate, betamethasone, dexamethasone, triamcinolone; pancreatic hormones, e.g., glucagon, insulin; parathyroid hormone, e.g., dihydrochysterol; thyroid hormones, e.g., calcitonin etidronate disodium, levothyroxine Na, liothyronine Na, liotrix, thyroglobulin, teriparatide acetate; antithyroid drugs; estrogenic hormones; progestins and antagonists, hormonal contraceptives, testicular hormones; gastrointestinal hormones: cholecystokinin, enteroglycan, galanin, gastric inhibitory polypeptide, epidermal growth factor-urogastrone, gastric inhibitory polypeptide, gastrin-releasing peptide, gastrins, pentagastrin, tetragastrin, motilin, peptide YY, secretin, vasoactive intestinal peptide, sincalide.

Enzymes. Hyaluronidase, streptokinase, tissue plasminogen activator, urokinase, PGE-adenosine deaminase.

Intravenous Anesthetics. Droperidol, etomidate, fetanyl citrate/droperidol, hexobarbital, ketamine HCl, methohexital Na, thiamylal Na, thiopental Na.

Antiepileptics. Carbamazepine, clonazepam, divalproex Na, ethosuximide, mephenytoin, paramethadione, phenytoin, primidone.

Peptides and proteins. The FcRn binding partners may be conjugated to peptides or polypeptides, e.g., ankyrins, arrestins, bacterial membrane proteins, clathrin, connexins, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor α, transforming growth factor β, interferon (IFN), and hormones, growth inhibitors, e.g., genistein, steroids etc; glycoproteins, e.g., ABC transporters, platelet glycoproteins, GPIb-IX complex, GPIIb-IIIa complex, vitronectin, thrombomodulin, CD4, CD55, CD58, CD59, CD44, lymphocye function-associated antigen, intercellular adhesion molecule, vascular cell adhesion molecule, Thy-1, antiporters, CA-15-3 antigen, fibronectins, laminin, myelin-associated glycoprotein, GAP, GAP-43. In this embodiment of the present invention, the polypeptide therapeutics may be covalently conjugated to the FcRn binding partner or the FcRn binding partner and therapeutic may be expressed as a fusion protein using standard recombinant genetic techniques, see Section 5.1.1 infra.

Cytokines and Cytokine Receptors. Examples of cytokines and receptors thereof which may be delivered via a FcRn binding parnter or conjugated to an FcRn binding partner in accordance with the present invention, include, but are not limited to: Interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, lymphokine inhibitory factor, macrophage colony stimulating factor, platelet derived growth factor, stem cell factor, tumor growth factor β, tumor necrosis factor, lymphotoxin, Fas, granulocyte colony stimulating factor, granulocyte macrophage colony stimulating factor, interferon α, interferon β, interferon γ.

Growth Factors and Protein Hormones. Examples of growth factors and receptors thereof and protein hormones and receptors thereof which may be delivered via a FcRn binding parnter or conjugated to an FcRn binding partner in accordance with the present invention, include, but are not limited to: erythropoietin, angiogenin, hepatocyte growth factor, fibroblast growth factor, keratinocyte growth factor, nerve growth factor, tumor growth factor α, thrombopoietin, thyroid stimulating factor, thyroid releasing hormone, neurotrophin, epidermal growth factor, VEGF, ciliary neurotrophic factor, LDL, somatomedin, insulin growth factor, insulin-like growth factor I and II.

Chemokines. Examples of chemokines and receptors thereof which may be delivered via a FcRn binding parnter or conjugated to an FcRn binding partner in accordance with the present invention, include, but are not limited to: ENA-78, ELC, GRO-α, GRO-β, GRO-γ, HRG, LIF, IP-10, MCP-1, MCP-2, MCP-3, MCP-4, MIP-1α, MIP-1β, MIG, MDC, NT-3, NT-4, SCF, LIF, leptin, RANTES, lymphotactin, eotaxin-1, eotaxin-2, TARC, TECK, WAP-1, WAP-2, GCP-1, GCP-2, α-chemokine receptors: CXCR1, CXCR2, CXCR3, CXCR4, CXCR5, CXCR6, CXCR7 β-chemokine receptors: CCR1, CCR2, CCR3, CCR4, CCR5, CCR6, CCR7.

Chemotherapeutics. The FcRn binding partners may be conjugated to chemotherapy or anti-tumor agents which are effective against various types of human cancers, including leukemia, lymphomas, carcinomas, sarcomas, myelomas etc., such as, doxorubicin, mitomycin, cisplatin, daunorubicin, bleomycin, actinomycin D, neocarzinostatin.

Antibodies. The FcRn binding partners of the present invention may be conjugated to antibodies including, but not limited to: (a) anti-cluster of differentiation antigen CD-1 through CD-166 and the ligands or counter receptors for these molecules; (b) anti-cytokine antibodies, e.g., anti-IL-1 through anti-IL-18 and the receptors for these molecules; (c) anti-immune receptor antibodies, antibodies against T cell receptors, major histocompatibility complexes I and II, B cell receptors, selectin killer inhibitory receptors, killer activating receptors, OX-40, MadCAM-1, Gly-CAM1, integrins, cadherens, sialoadherens, Fas, CTLA-4, Fcγ-receptors, Fcα-receptors, Fcε-receptors, Fcµ-receptors, and their ligands; (d) anti-metalloproteinase antibodies, e.g., collagenase, MMP-1 through MMP-8, TIMP-1, TIMP-2; anti-cell lysis/proinflammatory molecules, e.g., perforin, complement components, prostanoids, nitron oxide, thromboxanes; and (e) anti-adhesion molecules, e.g., carcioembryonic antigens, lamins, fibronectins.

Antiviral Agents. The FcRn binding partners may be conjugated to antiviral agents such as reverse transcriptase inhibitors and nucleoside analogs, e.g. ddI, ddC, 3TC, ddA, AZT; protease inhibitors, e.g., Invirase, ABT-538; inhibitors of in RNA processing, e.g., ribavirin.

Specific examples of known therapeutics which may be delivered via a FcRn binding partner include, but are not limited to:

(a) Capoten, Monopril, Pravachol, Avapro, Plavix, Cefzil, Duricef/Ultracef, Azactam, Videx, Zerit, Maxipime, VePesid, Paraplatin, Platinol, Taxol, UFT, Buspar, Serzone, Stadol NS, Estrace, Glucophage (Bristol-Myers Squibb);

(b) Ceclor, Lorabid, Dynabac, Prozac, Darvon, Permax, Zyprexa, Humalog, Axid, Gemzar, Evista (Eli Lily);

(c) Vasotec/Vaseretic, Mevacor, Zocor, Prinivil/Prinizide, Plendil, Cozaar/Hyzaar, Pepcid, Prilosec, Primaxin, Noroxin, Recombivax HB, Varivax, Timoptic/XE, Trusopt, Proscar, Fosamax, Sinemet, Crixivan, Propecia, Vioxx, Singulair, Maxalt, Ivermectin (Merck & Co.);

(d) Diflucan, Unasyn, Sulperazon, Zithromax, Trovan, Procardia XL, Cardura, Norvasc, Dofetilide, Feldene, Zoloft, Zeldox, Glucotrol XL, Zyrtec, Eletriptan, Viagra, Droloxifene, Aricept, Lipitor (Pfizer);

(e) Vantin, Rescriptor, Vistide, Genotropin, Micronase/Glyn./Glyb., Fragmin, Total Medrol, Xanax/alprazolam, Sermion, Halcion/triazolam, Freedox, Dostinex, Edronax, Mirapex, Pharmorubicin, Adriamycin, Camptosar, Remisar, Depo-Provera, Caverject, Detrusitol, Estring, Healon, Xalatan, Rogaine (Pharmacia & Upjohn);

(f) Lopid, Accrupil, Dilantin, Cognex, Neurontin, Loestrin, Dilzem, Fempatch, Estrostep, Rezulin, Lipitor, Omnicef, FemHRT, Suramin, Clinafloxacin (Warner Lambert).

Further examples of therapeutic agents which may be delivered by the FcRn binding partners of the present invention may be found in: Goodman and Gilman's The Pharmacological Basis of Therapeutics. 9th ed. McGraw-Hill 1996, incorporated herein by reference in its entirety.

5.4. Pharmaceutical Formulations for Vaccine Delivery

When administered, the conjugates of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents. Thus, "cocktails" including the conjugates and the agents are contemplated. The agents themselves may be conjugated to FcRn binding partners to enhance delivery of the agents across the epithelial barriers.

The conjugates of the invention may be administered in a purified form or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic-acid and salt (1–2% W/V); citric acid and a salt (1–3% W/V); boric acid and a salt (0.5–2.5% W/V); sodium bicarbonate (0.5–1.0% W/V); and phosphoric acid and a salt (0.8–2% W/V). Suitable preservatives include benzalkonium chloride (0.003–0.03% W/V); chlorbutanol (0.3–0.9% W/V); parabens (0.01–0.25% W/V) and thimerosal (0.004–0.02% W/V).

The term "carrier" as used herein, and described more fully below, means one or more solid or liquid filler, dilutants or encapsulating substances which are suitable for administration to a human or other mammal. The "carrier" may be an organic or inorganic ingredient, natural or synthetic, with which the active ingredient is combined to facilitate administration.

The components of the pharmaceutical compositions are capable of being commingled with the conjugates of the present invention, and with each other, in a manner such that there is no interaction which would substantially impair the desired pharmaceutical efficacy. The components of oral drug formulations include diluents, binders, lubricants, glidants, disintegrants, coloring agents and flavoring agents. Encapsulating substances for the preparation of enteric-coated oral formulations include cellulose acetate phthalate, polyvinyl acetate phthalate, hydroxypropyl methylcellulose phthalate and methacrylic acid ester copolymers. Solid oral formulations such as capsules or tablets are preferred. Elixirs and syrups also are well known oral formulations. The components of aerosol formulations include solubilized active ingredients, antioxidants, solvent blends and propellants for solution formulations, and micronized and suspended active ingredients, dispersing agents and propellants for suspension formulations. The oral, aerosol and nasal formulations of the invention can be distinguished from injectable preparations of the prior art because such formulations may be nonaseptic, whereas injectable preparations must be aseptic.

The term "adjuvant" is intended to include any substance which is incorporated into or administered simultaneously with the conjugates of the invention and which nonspecifically potentiates the immune response in the subject. Adjuvants include aluminum compounds, e.g., gels, aluminum hydroxide and aluminum phosphate, and Freund's complete or incomplete adjuvant (in which the conjugate is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U) leutinan, pertussis toxin, cholera toxin, lipid A, saponins and peptides, e.g. muramyl dipeptide. Rare earth salts, e.g., lanthanum and cerium, may also be used as adjuvants. The amount of adjuvants depends on the subject and the particular conjugate used and can be readily determined by one skilled in the art without undue experimentation.

Other supplementary immune potentiating agents, such as cytokines, may be delivered in conjunction with the conjugates of the invention. The cytokines contemplated are those that will enhance the beneficial effects that result from administering the immunomodulators according to the invention. Cytokines are factors that support the growth and maturation of cells, including lymphocytes. It is believed that the addition of cytokines will augment cytokine activity stimulated in vivo by carrying out the methods of the invention. The preferred cytokines are interleukin (IL)-1, IL-2, gamma-interferon and tumor necrosis factor α. Other useful cytokines are believed to be IL-3, IL-4, IL-5, IL-6, IL-7, IL-8, IL-9, IL-10, IL-11, IL-12, IL-13, erythropoietin, leukemia inhibitory factor, oncostatin-M, ciliary neurotrophic factor, growth hormone, prolactin, CD40-ligand, CD27-ligand, CD30-ligand, alpha-interferon, beta-interferon, and tumor necrosis factor-β. Other cytokines known to modulate T-cell activity in a manner likely to be useful according to the invention are colony stimulating factors and growth factors including granulocyte and/or macrophage stimulating factors (GM-CSF, G-CSF and CSF-1) and platelet derived, epidermal, insulin-like, transforming and fibroblast growth factors. The selection of the particular cytokines will depend upon the particular modulation of the immune system that is desired. The activity of cytokines on particular cell types is known to those of ordinary skill in the art.

The precise amounts of the foregoing cytokines used in the invention will depend upon a variety of factors, including the conjugate selected, the dose and dose-timing selected, the mode of administration and the characteristics of the subject. The precise amounts selected can be determined without undue experimentation, particularly since a threshold amount will be any amount which will enhance the desired immune response. Thus, it is believed that nanogram to milligram amounts are useful, depending upon the mode of delivery, but that nanogram to microgram amounts are likely to be most useful because physiological levels of cytokines are correspondingly low.

The preparations of the invention are administered in effective amounts. An effective amount is that amount of a conjugate that will alone, or together with further doses, stimulate an immune response as desired. This may involve the stimulation of a humoral antibody response resulting in an increase in antibody titer in serum, improved mucosal immunity, a clonal expansion of cytotoxic T lymphocytes or tolerance to an antigen, including a self antigen. It is believed that doses ranging from 1 nanogram/kilogram to 100 milligrams/kilogram, depending upon the mode of administration, will be effective. The preferred range is believed to be between about 500 nanograms and 500 micrograms/kilogram, and most preferably between 1 microgram and 100 micrograms/kilogram. The absolute amount will depend upon a variety of factors, including the conjugate selected, the immune modulation desired, whether the administration is in a single or multiple doses, and individual patient parameters including age, physical condition, size and weight. For treatment of a subject with a tumor the size, type, location and metastases of the tumor may be factored in when determining the amount of conjugate to administer. These factors are well known to those of ordinary skill in the art and can be addressed with no more than routine experimentation.

A variety of administration routes are available. The particular mode selected will depend, of course, upon the particular conjugate selected, the particular condition being treated and the dosage required for therapeutic efficacy. The methods of this invention, generally speaking, involve delivering the conjugates of the invention to an epithelial surface. Preferred modes of administration are oral, intrapulmonary, intrabiliary and intranasal.

Compositions may be conveniently presented in unit dosage form and may be prepared by any of the methods well known in the art of pharmacy. All methods include the step of bringing the conjugate into association with a carrier which constitutes one or more accessory, ingredients. In general, the compositions are prepared by uniformly and intimately bringing the conjugate into association with a liquid carrier, a finely divided solid carrier, or both, and then, if necessary, shaping the product.

Other delivery systems can include time-release, delayed release or sustained release delivery systems. Such systems can avoid repeated administrations of the conjugates of the invention, increasing convenience to the subject and the physician. Many types of release delivery systems are available and known to those of ordinary skill in the art. They include polymer based systems such as polylactic and polyglycolic acid, polyanhydrides and polycaprolactone; wax coatings, compressed tablets using conventional binders and excipients, and the like. Bioadhesive polymer systems to enhance delivery of a material to the intestinal epithelium are known and described in published PCT application WO 93/21906. Capsules for delivering agents to the intestinal epithelium also are described in published PCT application WO 93/19660.

5.5. Pharmaceutical Formulations for Administration of Therapeutics

The pharmaceutical formulation of the invention contain the FcRn binding partner conjugate as the active ingredient in a pharmaceutically acceptable carrier suitable for administration and delivery in vivo. In preferred embodiments the pharmaceutical compositions of the present invention are formulated for oral, sublingual, buccal, intranasal and administration by inhalation.

When administered, the conjugates of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents. Thus, "cocktails" including the conjugates and the agents are contemplated. The agents themselves may be conjugated to FcRn binding partners to enhance delivery of the agents across the epithelial barriers.

5.5.1. Dosages

The preferred amount of FcRn binding partner conjugates in all pharmaceutical preparations made in accordance with the present invention should be a therapeutically effective amount thereof which is also a medically acceptable amount thereof. Actual dosage levels of FcRn binding partner conjugates in the pharmaceutical compositions of the present invention may be varied so as to obtain an amount of FcRn binding partner conjugates which is effective to achieve the desired therapeutic response for a particular patient, pharmaceutical composition of FcRn binding partner conjugates, and mode of administration, without being toxic to the patient.

The selected dosage level and frequency of administration will depend upon a variety of factors including the route of administration, the time of administration, the rate of excretion of the therapeutic agent(s) including FcRn binding partner conjugates, the duration of the treatment, other drugs, compounds and/or materials used in combination with FcRn binding partner conjugates, the age, sex, weight, condition, general health and prior medical history of the patient being treated and the like factors well known in the medical arts. For example, the dosage regimen is likely to vary with pregnant women, nursing mothers and children relative to healthy adults.

A physician having ordinary skill in the art can readily determine and prescribe the therapeutically effective amount of the pharmaceutical composition required. For example, the physician could start doses of FcRn binding partner conjugates employed in the pharmaceutical composition of the present invention at levels lower than that required to achieve the desired therapeutic effect and gradually increase the dosage until the desired effect is achieved.

5.5.2. Pharmaceutical Formulations

The pharmaceutical compositions of the present invention, including the FcRn binding partners conjugated to a therapeutic as the active agent are suitable preferably for oral, sublingual, and intranasal delivery. The pharmaceutical compositions are suitable for the delivery of the FcRn binding partner conjugates to epithelial barriers. The pharmaceutical compositions may also be formulated to be suitable for parenteral, transdermal, intradermal and intravenous delivery.

The pharmaceutical compositions, containing biologically active FcRn binding partner conjugates as the active agent, that are suitable for transmucosal delivery via oral cavity delivery are in the form of a solid as lingual, buccal or sublingual tablets, troches (lozenges), powders, time-release granules, pellets or the like may also be used, or in the form of a liquid as a liquid drop or drops, aerosol spray or mist, applied sublingually (under the tongue), on top of the tongue, or buccally (between the cheek and gingiva). The rate of oral mucosal membrane absorption of FcRn binding partner conjugates, is controlled by the specific liquid or solid dosage formulation selected. Specific formulations allow the process of absorption to take place over a sustained, but relatively short period of time, allowing for a gradual build up and constant blood level of the FcRn binding partner conjugates.

For prolonged delivery, the active ingredient can be formulated as a depot preparation, for administration by implantation; e.g., subcutaneous, intradermal, or intramuscular injection. Thus, for example, the active ingredient may be formulated with suitable polymeric or hydrophobic materials (e.g., as an emulsion in an acceptable oil) or ion exchange resins, or as sparingly soluble derivatives; e.g., as a sparingly soluble salt form of the FcRn binding partner conjugate.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound. By way of example, but not by limitation, the FcRn binding partners may be conjugated to the following therapeutics for epithelial barrier targeted delivery:

For buccal or sublingual administration, the compositions may take the form of tablets or lozenges formulated in conventional manner. For rectal and vaginal routes of administration, the active ingredient may be formulated as solutions (for retention enemas) suppositories or ointments.

For administration by inhalation, the active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

6. EXAMPLES

Materials

Abbreviations

BSA, bovine serum albumin; cDNA, complementary deoxyribonucleic acid; CT-B, cholera toxin B subunit; DMEM, Dulbecco's modified Eagle's medium; DMSO, dimethyl sulfoxide; DOC, desoxycholate; ECL, enhanced chemiluminescence; ELISA, enzyme linked immunosorbent assay; HBSS, Hanks' balanced salt solution without calcium or magnesium; HEPES, N-[2-hydroxyethyl]piperazine-N'-[2-ethanesulfonic acid]; hGH, human growth hormone; IEC, intestinal epithelial cells; KI, potassium iodide; MHC, major histocompatibility complex; NaOH, sodium hydroxide; $NH_4Cl$, ammonium chloride; NHS-rhodamine, N-hydroxysuccinimidyl-rhodamine; RNA, ribonucleic acid; RT-PCR, reverse transcriptase-polymerase chain reaction; SATA, N-succinimdyl S-acetylthioacetate; SDS-PAGE, sodium dodecyl sulfate-polyacrylamide gel electrophoresis; sulfo-LC-SPDP, sulfosuccinimidyl 6-[3-(2-pyridyldithio)propionamide]hexanote; sulfo-NHS-biotin, sulfosuccinimidobiotin; sulfo-SMCC, sulfosuccinimidyl 4-(N-maleimidoriethyl)cyclo-hexane-1-carboxylate.

Chemicals cDNA Cycle Kits was purchased from Invitrogen (San Diego, Calif.). Taq polymerase was purchased from Perkin-Elmer Cetus (Norwalk, Conn.). CircumVent™ Kits were purchased from New England Biolabs (Beverly, Mass.). Radionucleotides and radioactive chemicals were purchased

Example 1

Expression of FcRn mRNA in Human Intestinal Epithelial Primary Cells and Cell Lines Total RNA was extracted from adult human enterocytes by standard methodology well known in the art (Sambrook et al., ibid.). One microgram of RNA from each cell type was used as a template to prepare the cDNA substrate for reverse transcriptase-polymerase chain reaction (RT-PCR) using a cDNA Cycle Kit (invitrogen, San Diego, Calif.). Thirty cycles of PCR were performed on the cDNA using Taq polymerase (Perkin-Elmer Cetus, Norwalk, Conn.) according to the manufacturer's instructions using primers TGCTGGGCTGTGAACTG and CGCTTTTAGCAGTCGGAA. The PCR cycle conditions were: denaturation at 94° C. for one minute, annealing at 55° C. for two minutes and extension at 72° C. for three minutes. Amplification products were resolved by electrophoresis on a 1.5% agarose gel and visualized by ethidium bromide staining, which showed the presence of the expected approximately 800 base pair amplification product in all samples except the adult colonic epithelial cells. To confirm the identity of the RT-PCR amplification product, the DNA band was excised from the agarose gel, subcloned into pCR 11 (Invitrogen, San Diego, Calif.) and sequenced using a Prismdye-deoxy terminator cycle sequencing kit (Applied Biosystems, Foster City, Calif.) using primers from both vector and human FcRn sequence. Reaction products were analyzed on an Applied Biosystems sequencer. The sequence of the amplification products exactly matched the FcRn gene sequence, confirming the identity of the expressed gene.

Example 2

Detection of FcRn mRNA by Northern Blot

To confirm the expression of FcRn in human intestinal epithelial cells and cell lines, a Northern blot was prepared using the RNA samples prepared as described in Example 1 from adult human enterocytes, and from two human adenocarcinoma cell lines of colonic origin, CaCO-2 and HT-29. The RNA samples were resolved by formaldehyde/agarose gel electrophoresis and transferred to a nylon membrane by standard procedures (Sambrook et al., *Molecular Cloning: A Laboratory Manual*, Cold Spring Harbor Press, Cold Spring Harbor, N.Y. 1989). The membrane was probed using a $^{32}$P-radiolabeled 120 base pair probe from the 3' untranslated region of FcRn by standard methods. Autoradiograms of the Northern blot demonstrated the presence of the 1.5 kilobase hFcRn transcript in the enterocytes and both cell lines. Therefore, the expression of FcRn in human adult intestinal epithelial cells and cell lines was demonstrated by two different methods of RNA detection.

Example 3

Labeling and Immunoprecipitation of the MHC-Class I Related Fc Receptor (FcRn) from Intestinal Epithelial Cells The expression of FcRn in human intestinal epithelial cells was confirmed by immunoprecipitation of the protein. Caco-2 cells were labeled metabolically using IIS-methionine (DuPont/NEN, Boston, Mass.) and proteins were extracted by methods well known in the art (Harlow and Lane, *Antibodies: A Laboratory Manual*). A polyclonal rabbit anti-rat MHC class I related FcR heavy chain specific antiserum bound to protein-A-sephorose was used to immunoprecipitate FcRn from the cell extracts using standard methods (FcRn can be purified by well established methods, Simister and Rees 1985, European J. Immunology, 15:733–8, and used to Immunize rats followed by collection of serum, Harlow and Lane, supra.). Immunoprecipitates were resolved by SDS-PAGE and visualized by autoradiography. A 48 kilodalton FcRn protein was observed, confirming expression observed at the RNA level.

Example 4

Expression of FcRn Protein on the Cell Surface of Human Intestinal Epithelial Cells About $3\times10^7$ HT-29 intestinal epithelial cells were detached from tissue culture plates by nonenzymatic methods and were washed four times with ice cold Hanks' balanced salt solution containing no calcium or magnesium (HBSS-, GIBCO/Life Technologies, Gaithersburg, Md.). To label cell surface proteins, the washed cells were incubated twice for 20 minutes with 1.5 mi of 0.5 mg/mi sulfo-NHS-biotin (Pierce, Rockford, Ill.) in DMSO. Labeled cells were washed five times with 50 mM NH$_4$C, incubated 20 minutes with 10 ml of RPMI 1640 (Cellgro, City, State) containing 1 mM L-glutamine (Mediatech, Washington, D.C.), and washed four times with HBSS-.

The cells were lysed, then precleared overnight with protein A-Sepharose beads (Pharmacia Biotech, Piscataway, N.J.) using standard techniques well known in the art. SDS and desoxycholic acid (DOC) were added to the supernatants to final concentrations of 0.1% and 0.5%, respectively. Lysates were precleared with normal rabbit serum and immunoprecipitated with polyclonal rabbit anti-rat MHC class I related FcR antibody by methods well known in the art. Immunoprecipitates were resolved by SDS-PAGE and transferred to nitrocellulose membranes. The nitrocellulose membrane was processed for incubation with 1:10,000 diluted streptavidinhorseradish peroxidase (Pierce, Rockford Ill.) as recommended by the manufacturer. The membrane was then processed for detection of bound horseradish peroxidase using an ECL kit (Amersham, Arlington Heights, Ill.). Light emitted by cleavage of the chemiluminescent substrate was detected by exposure of the membrane to light-sensitive film. The film exposures showed that FcRn was expressed on the surface of HT-29 intestinal epithelial cells.

Example 5

Functional Activity of Human FcRn on the Cell Surface of Intestinal Epithelial Cells To show that the FcRn expressed on the cell surface of intestinal epithelial cells was functional, Caco-2 cells and human adult jejunal intestinal epithelial cells (IECs) were tested for the ability to bind Fc fragment of antibody. Caco-2 and jejunal IECs were distributed to microcentrifuge tubes ($2 \times 10^6$ cells per tube) and pelleted at 2000 rpm for 2–3 minutes at 4° C. Cell pellets were washed once in DMEM containing 20 mM HEPES, pH 6.0 or pH 8.0 at 4° C. and resuspended in 0.2 ml of the same medium. The cell suspensions were transferred to 12 well plates for assay. $^{125}$I-Fc fragment (200 ng/ml, $4 \times 10^{-9}$M) in DMEM containing 20 mM HEPES, 1.0 mM KI and 0.1 % fish gelatin, pH 6.0 or pH 8.0 with or without 0.5 mg/ml unlabeled human IgG ($3.3 \times 10^{-6}$M) was added to each well. The cells were allowed to bind IgG or Fc at 37° C. for two hours in a 5% $CO_2$ humidified atmosphere. Cells were transferred to microcentrifuge tubes and pelleted at 2000 rpm for 2–3 minutes at 4° C. Unbound $^{125}$I-Fc was removed by washing the cell pellets once with cold DMEM containing 20 mM HEPES, pH 6.0 or pH 8.0 at 40° C. Cells were disrupted in 0.5 ml 0.1 M NaOH and the resulting solution transferred to scintillation vials. $^{125}$I was quantified using a CliniGanima 1272 gamma counter (LKB Wallac, Piscataway, N.J.). Both Caco-2 cells and human adult jejunum IEGs specifically bound $^{125}$I-Fc at pH 6.0 but not at pH 8.0, demonstrating functional pH-dependent binding as observed for rat neonatal FcRn and cloned human FcRn (Story et al., *J. Exp. Med.* 180: 2377–2381; December 1994).

Example 6

Preparation of Human Immunoglobulin G

Non-specific purified immunoglobulin G from human, mouse, rat, goat, pig, cow, and other species may be purchased from commercial vendors such as Sigma Chemical Co., Pierce Chemical, HyClone Laboratories, ICN Biomedicals and Organon Teknika-Cappei.

Immunoglobulin G also may be isolated by ammonium sulfate precipitation of precipitation of blood serum. The protein precipitate is further fractionated by ion exchange chromatography or gel filtration chromatography, to isolate substantially purified non-specific IgG. By non-specific IgG it is meant chat no single specificity within the antibody population or pool is dominant.

Immunoglobulin G also may be purified from blood serum by adsorption to protein A attached to a solid support such as protein A-Sepharose (Pharmacia), AvidChrom-Protein A (Sigma), or protein G-Sepharose (Sigma). Other methods of purification of IgG are well known to persons skilled in the art and may be used for the purpose of isolation of non-specific IgG.

Example 7

Preparation of Human Lmmuglobulin G

To prepare the Fc fragments of human IgG, IgG isolated as in example 6 is subjected to digestion with immobilized papain (Pierce) according to the manufacturer's recommended protocol. Other proteases that digest IgG to produce intact Fc fragments that can bind to Fc receptors, e.g. plasmin (Sigma) or immobilized ficin (Pierce), are known to skilled artisans and may be used to prepare Fc fragments. The digested immunoglobulin then is incubated with an affinity matrix such as protein A-Sepharose or protein G-Sepharose. Non-binding portions of IgG are eluted from the affinity matrix by extensive washing in batch or column format. Fc fragments of IgG then are eluted by addition of a buffer that is incompatible with Fc-adsorbent binding. Other methodologies effective in the purification of Fc fragments also may be employed.

Example 8

Conjugation of Compounds to Human Immunoglobulin Fc-Fragments

To deliver compounds via the FcRn transport mechanism, such compounds can be coupled to whole IgG or Fc fragments. The chemistry of cross-linking and effective reagents for such purposes are well known in the art. The nature of the crosslinking reagent used to conjugate whole IgG or Fc fragments and the compound to be delivered is not restricted by the invention. Any crosslinking agent may be used provided that a) the activity of the compound is retained, and b) binding by the FcRn of the Fc portion of the conjugate is not adversely affected.

An example of an effective one-step crosslinking of Fc and a compound is oxidation of Fc with sodium periodate in sodium phosphate buffer for 30 minutes at room temperature, followed by overnight incubation at 4° C. with the compound to be conjugated. Conjugation also may be performed by derivatizing both the compound and Fc fragments with suffosuccinimidyl 6-[3-(2-pyridyldithio)propionamidel hexanoate (sulfo-LC-SPDP, Pierce) for 18 hours at room temperature. Conjugates also may be prepared by derivatizing Fc fragments and the desired compound to be delivered with different crosslinking reagents that will subsequently form a covalent linkage. An example of this reaction is derivatization of Fc fragments with sulfosuccinimidyl 4-(N-maleimidomethyl)cyclo-hexane-1-carboxylate (Sulfo-SMCC, Pierce) and the compound to be conjugated to Fc is thiolated with N-succinimidyl S-acetylthioacetate (SATA). The derivatized components are purified free of crosslinker and combined at room temperature for one hour to allow crosslinking. Other crosslinking reagents comprising aldehyde, imide, cyano, halogen, carboxyl, activated carboxyl, anhydride and maleimide functional groups are known to persons of ordinary skill in the art and also may be used for conjugation of compounds to Fc fragments. The choice of cross-linking reagent will, of course, depend on the nature of the compound desired to be conjugated to Fc. The crosslinking reagents described above are effective for protein-protein conjugations. If the compound to be conjugated is a carbohydrate or has a carbohydrate moiety, then heterobifunctional crosslinking reagents such as ABH, M2C2H, MPBH and PDPH are useful for conjugation with a proteinaceous FcRn binding molecule (Pierce Chemical Co., Rockford, Ill.). Another method of conjugating proteins and carbohydrates is disclosed by Brumeanu et al. (Genetic Engineering News, Oct. 1, 1995, p. 16). If the compound to be conjugated is a lipid or has a lipid moiety which is convenient as a site of conjugation for the FcRn binding molecule, then crosslinkers such as SPDP, SMPB and derivatives thereof may be used (Pierce Chemical Co., Rockford, Ill.). It is also possible to conjugate any molecule which is to be delivered by noncovalent means. One convenient way for achieving noncovalent conjugation is to raise antibodies to the compound to be delivered, such as monoclonal antibodies, by methods well known in the art, and select a monoclonal antibody having the correct Fc region and desired antigen binding properties. The antigen to be delivered is then prebound to the monoclonal antibody carrier. In all of the above crosslinking reactions it is important to purify the derivatized compounds free of crosslinking reagent. It is important also to purify the final conjugate substantially free of unconjugated reactants. Purification may be achieved by affinity, gel filtration or ion exchange chromatography based on the properties of either component of the conjugate. A particularly preferred method is an initial affinity purification step using protein A-Sepharose to retain Fc and Fc-compound conjugates, followed by gel filtration or ion exchange chromatography based on the mass, size or charge of the Fc conjugate. The initial step of this purification scheme ensures that the conjugate will bind to FcRn which is an essential requirement of the invention.

Example 9

IgG-Facilitated Delivery of Foreign Antigen Across the Intestinal Epithelial Barrier To test the ability of Fc binding partner-antigen conjugates to be transported across epithelial barriers, foreign antigens are conjugated to IgG molecules for administration to mice. A convenient foreign antigen is the fluorescent dye rhodamine, since it may be visualized in frozen semi-thin sections of intestinal epithelium. Rhodamine is covalently linked to non-specific mouse IgG, prepared as described in Example 6, cholera toxin B subunit (Sigma) and ovalbumin (Sigma) by incubation with succinyl-rhodamine (Molecular Probes, Eugene, Oreg.) as recommended by the manufacturer. The IgG-rhodamine conjugate is purified by protein G-Sepharose affinity chromatography. After dialysis to remove unconjugated succinyl-rhodamine, cholera toxin B (CT-B)-rhodamine and ovalbumin-rhodamine conjugates are purified by gel filtrations or ion exchange chromatography. Fractions of the eluate are assayed for the presence of conjugates by determining fluorescence. Functional binding of the IgG and CT-B subunit conjugates may be tested by binding to FcRn and ganglioside GM1, respectively. Cholera toxin B-rhodamine and ovalbuminrhodamine serve as positive and negative controls, respectively.

Balb/c mice are administered 0.2 nanomoles of the three rhodamine conjugates described above, with or without 0.2 nanomoles unlabeled cholera toxin as a non-specific adjuvant, by intragastric administration in the presence of 75 micromoles $NaHCO_3$ and 20 mg/mi soybean trypsin inhibitor to inhibit gastric degradation. After 6 hours the mice are sacrificed and intestine is removed, frozen and processed for semi-thin sectioning. Sections of the intestinal epithelium are illuminated on a fluorescent microscope and examined for intracellular fluorescence. The presence of fluorescence in intestinal epithelial cells of mice fed IgG-rhodamine indicates that the IgG conjugates are effectively transported in an apical to basolateral direction across the intestinal epithelial barrier. FcRn is capable of transporting immunogens as conjugates with FcRn binding partners.

Example 10

Mouse Mucosal Immune Response to Orally Delivered Antigen-IgG Conjugate Via FcRn-Mediated Transcytosis Transgenic mice homozygous for deletion of β2-microglobulin (a critical component of Fc-receptor function) and their normal wild-type litter mates are used for studies of generation of a mucosal immune response. If rhodamine-IgG elicits a mucosal immune response by binding to apical membrane Fc receptors, a positive immune response should be found in wild-type but not β2-microglobulin "knockout" mice. In contrast, rhodamine-cholera toxin B subunit (CT-6) should elicit a positive immune response in both wild type and—knockout" mice as transcytosis of CT-6 across the epithelial barrier is not dependent on binding to apical membrane Fc receptors. Rhodamine-ovalbumin does, not enter transcytotic vesicles (but may enter intestinal epithelia by fluid phase endocytosis) and should not elicit an immune response in any mice.

Three groups of wild type and $β_2$-microglobulin knockout mice are orally immunized with the three rhodamine conjugates described in Example 9. Parallel experiments are conducted with the addition of 0.2 nanomoles of cholera toxin as non-specific adjuvant. Equimolar quantities of the rhodamine conjugates are administered intragastrically. The mice are "immunized" by this method every ten days for a total of three times. Two weeks after the third oral immunization the mice are sacrificed and the rhodamine-specific immune response is determined by ELISA on gut secretions and serum by standard methodology. Anti-rhodamine serum immunoglobulins are most evident in the wild type mice fed rhodamine conjugates of CT-B and IgG. Knockout mice lacking $β_2$-microglobulin generate a mucosal immune response to rhodamine-CT-B but not to rhodamine-IgG, indicating that receptor-mediated transcytosis plays an essential role in the mucosal immune response. The control rhodamine-ovalbumin conjugate elicits little or no immune response in either the wild type or the $β_2$-microglobulin knockout mice.

Example 11

IgG-Facilitated Delivery of the Bioactive Substance Insulin, Across the Intestinal Epithelial Barrier To test the ability of Fc binding partner-bioactive substance conjugates to be transported across epithelial barriers, the bioactive substance, insulin is conjugated to IgG molecules for administration to mice. A convenient therapeutic agent to be delivered is insulin, as its presence in systemic circulation can be determined by measuring a decrease in blood glucose levels. The results of such an assay demonstrate the efficacy of the FcRn binding partner delivery system. Insulin is covalently linked to non-specific mouse IgG, prepared as described in Example 6, cholera toxin B subunit (Sigma) and ovalbumin (Sigma) by incubation with succinyl-insulin (Molecular Probes, Eugene, Oreg.) as recommended by the manufacturer. The IgG-insulin conjugate is purified by protein G-Sepharose affinity chromatography. After dialysis to remove unconjugated succinyl-Insulin, cholera toxin B (CT-B)-Insulin and ovalbumin-Insulin conjugates are purified by gel filtrations or ion exchange chromatography. Fractions of the eluate are assayed for the presence of conjugates by determining fluorescence. Functional binding of the IgG and CT-B subunit conjugates may be tested by binding to FcRn and ganglioside GM1, respectively. Cholera toxin B-Insulin and ovalbumin Insulin serve as positive and negative controls, respectively.

Balb/c mice are administered 0.2 nanomoles of the three Insulin cojugates described above, with or without 0.2 nanomoles unlabeled cholera toxin as a non-specific control, by oral administration in the presence of 75 micromoles NaHCO$_3$ and 20 mg/mi soybean trypsin inhibitor to inhibit gastric degradation.

In Vivo Insulin Delivery

Balb/C mice of female sex were fasted for 12 hours before experiment. Each mouse was gavaged 200 µL of each preparation as described in Table 9.3. Food was restored immediately after administration. Blood samples for glucose determination was drawn from mouse tail vein under methoxyflurane anesthesia. Samples were drawn right before the administration (0 hour), as well as at 1, 2, 3 and 3.5 hours post administration of each preparation. Blood glucose level was measured using a One Touch® Profile Diabetes Tracking System (Lifescan, Milpitas, Calif.) with one Touch® Test strips, by applying blood to form a round drop which completely covered the test spot on the test strip. Readings (in mg/dL) were obtained from the meter indicating the blood glucose level detected.

The invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

All references cited herein are incorporated herein by reference for all purposes.

Those skilled in the art will be able to recognize or ascertain with no more than routine experimentation numerous equivalents to the specific products and processes described above. Such equivalents are considered to be within the scope of the invention and are intended to be covered by the following claims in which we claim:

The invention claimed is:

1. A pharmaceutical preparation for application to an apical surface of an epithelial barrier comprising:
a conjugate of a cytokine and an FcRn binding partner, and
a pharmaceutically acceptable carrier, wherein the preparation is formulated as an aerosol formulation comprising a propellant.

2. The pharmaceutical preparation of claim 1, wherein the FcRn binding partner is non-specific IgG or an FcRn binding fragment of IgG.

3. The pharmaceutical preparation of claim 1, wherein the FcRn binding partner is an Fc fragment of IgG.

4. The pharmaceutical preparation of claim 1, wherein the cytokine is covalently coupled to the FcRn binding partner.

5. The pharmaceutical preparation of claim 4, wherein the cytokine is erythropoietin.

6. The pharmaceutical preparation of claim 4, wherein the cytokine is α, β, or γ-interferon.

7. The pharmaceutical preparation of claim 6, wherein the cytokine is β interferon.

8. The pharmaceutical preparation of claim 4, wherein the cytokine is an interleukin selected from the group IL-1, IL-2, IL-3, IL-4, IL-5, IL-6, IL-7, IL-8, IL-9, IL-10, IL-11, IL-12, IL-13, IL-14, IL-15, IL-16, IL-17, and IL-18.

9. The pharmaceutical preparation of claim 4, wherein the cytokine is tumor necrosis factor.

10. The pharmaceutical preparation of claim 4, wherein the cytokine is a colony-stimulating factor.

11. The pharmaceutical preparation of claim 4, wherein the cytokine is a growth factor.

12. The pharmaceutical preparation of claim 1, wherein the preparation is nonaseptic.

13. The pharmaceutical preparation of claim 1, wherein the aerosol formulation comprises (a) a powder mix comprising the conjugate and a powder base, and (b) the propellant.

14. A pharmaceutical preparation for application to an apical surface of an epithelial barrier comprising:

an inhaler or insufflator containing (a) a powder mix comprising a conjugate of a cytokine and an FcRn binding partner, and a powder base; and (b) a propellant.

15. The pharmaceutical preparation of claim 14, wherein the powder mix is contained in a capsule or cartridge.

16. The pharmaceutical preparation of claim 14, wherein the powder base is lactose.

17. The pharmaceutical preparation of claim 14, wherein the FcRn binding partner is non-specific IgG or an FcRn binding fragment of IgG.

18. The pharmaceutical preparation of claim 14, wherein the FcRn binding partner is an Fc fragment of IgG.

19. The pharmaceutical preparation of claim 14, wherein the cytokine is covalently coupled to the FcRn binding partner.

20. The pharmaceutical preparation of claim 19, wherein the cytokine is erythropoietin.

21. The pharmaceutical preparation of claim 19, wherein the cytokine is α, β, or γ-interferon.

22. The pharmaceutical preparation of claim 21, wherein the cytokine is β interferon.

23. The pharmaceutical preparation of claim 19, wherein the cytokine is an interleukin selected from the group IL-1, IL-2, IL-3, IL-4, IL-5, IL-6, IL-7, IL-8, IL-9, IL-10, IL-11, IL-12, IL-13, IL-14, IL-15, IL-16, IL-17, and IL-18.

24. The pharmaceutical preparation of claim 19, wherein the cytokine is tumor necrosis factor.

25. The pharmaceutical preparation of claim 19, wherein the cytokine is a colony-stimulating factor.

26. The pharmaceutical preparation of claim 19, wherein the cytokine is a growth factor.

27. The pharmaceutical preparation of claim 14, wherein the preparation is nonaseptic.

28. The pharmaceutical preparation of claim 14, wherein the powder base is starch.

* * * * *

UNITED STATES PATENT AND TRADEMARK OFFICE
CERTIFICATE OF CORRECTION

PATENT NO. : 7,067,129 B2
APPLICATION NO. : 10/215298
DATED : June 27, 2006
INVENTOR(S) : Richard S. Blumberg et al.

It is certified that error appears in the above-identified patent and that said Letters Patent is hereby corrected as shown below:

On the Title Page, Item (54) In the Title, "IN" should read --OF--.

Signed and Sealed this

Twenty-sixth Day of September, 2006

JON W. DUDAS
*Director of the United States Patent and Trademark Office*